(12) United States Patent
Suresh et al.

(10) Patent No.: US 12,390,291 B2
(45) Date of Patent: Aug. 19, 2025

(54) DECOUPLING TOOL SHAFT FROM CABLE DRIVE LOAD

(71) Applicant: Intuitive Surgical Operations, Inc., Sunnyvale, CA (US)

(72) Inventors: Ashwinram Suresh, San Jose, CA (US); Grant M. Kadokura, San Diego, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 995 days.

(21) Appl. No.: 17/293,460

(22) PCT Filed: Nov. 15, 2019

(86) PCT No.: PCT/US2019/061883
§ 371 (c)(1),
(2) Date: May 12, 2021

(87) PCT Pub. No.: WO2020/102776
PCT Pub. Date: May 22, 2020

(65) Prior Publication Data
US 2021/0401524 A1    Dec. 30, 2021

Related U.S. Application Data

(60) Provisional application No. 62/767,885, filed on Nov. 15, 2018.

(51) Int. Cl.
*A61B 34/00*    (2016.01)
*A61B 34/35*    (2016.01)
(Continued)

(52) U.S. Cl.
CPC .............. *A61B 34/71* (2016.02); *A61B 34/35* (2016.02); *A61B 34/37* (2016.02); *A61B 34/76* (2016.02);
(Continued)

(58) Field of Classification Search
CPC ......... A61B 34/71; A61B 34/35; A61B 34/37; A61B 34/76; A61B 34/77; A61B 90/50;
(Continued)

(56) References Cited

U.S. PATENT DOCUMENTS 2,186,181 A    1/1940    Gustav et al.
2,537,339 A    1/1951    Meyer et al.
(Continued)

FOREIGN PATENT DOCUMENTS

CA    3039534 A1    4/2018
CN    103717355 A    4/2014
(Continued)

OTHER PUBLICATIONS

Hazel., "Comparing Strain Gage Measurements to Force Calculations in a Simple Cantilever Beam," Worcester Polytechnic Institute Major Qualifying Project, 39 pages (Jan. 27, 2016).
(Continued)

*Primary Examiner* — Tan-Uyen T Ho
*Assistant Examiner* — David P Stein

(57) ABSTRACT

A surgical tool is provided that includes a hollow shaft and a cable extending within the shaft such that the cable is isolated from external forces imparted to the shaft; the shaft and a carriage are included as links of a 4-bar linkage that also includes first and second side links that are rotatably mounted to the carriage at respective first and second distal pivot axes and that are rotatably mounted to the shaft at respective first and second proximal pivot axes; the segment of the cable extends between a distal pulley rotatably at the carriage and a proximal pulley rotatably mounted at the shaft and a segment of the cable extends within the shaft; a distance between the first distal and first proximal pivot axes matches a distance between an axis of the distal pulley axis and an axis of the proximal pulley such that a rocking
(Continued)

motion of the 4-bar linkage due to external force upon the shaft exerts no force upon the cable.

21 Claims, 12 Drawing Sheets

(51) Int. Cl.
    *A61B 34/37*         (2016.01)
    *A61B 90/50*         (2016.01)

(52) U.S. Cl.
    CPC .............. *A61B 34/77* (2016.02); *A61B 90/50* (2016.02); *A61B 2034/715* (2016.02); *A61B 2090/506* (2016.02)

(58) Field of Classification Search
    CPC ........ A61B 2034/715; A61B 2090/506; A61B 34/70; A61B 2034/305; A61B 34/30
    See application file for complete search history.

(56) References Cited

U.S. PATENT DOCUMENTS

| | | |
|---|---|---|
| 2,906,143 A | 9/1959 | Musser |
| 3,325,761 A | 6/1967 | Mclellan |
| 3,358,511 A | 12/1967 | Bargen |
| 3,618,420 A | 11/1971 | Horwitt et al. |
| 4,064,758 A | 12/1977 | Harrison |
| 4,146,864 A | 3/1979 | Bethe |
| 4,341,144 A | 7/1982 | Milne |
| 4,507,170 A | 3/1985 | Myhre |
| 4,728,137 A | 3/1988 | Hamed et al. |
| 5,024,107 A | 6/1991 | Bethe |
| 5,333,504 A | 8/1994 | Lutz et al. |
| 5,625,576 A | 4/1997 | Massie et al. |
| 5,784,542 A | 7/1998 | Ohm et al. |
| 5,792,135 A | 8/1998 | Madhani et al. |
| 5,855,583 A | 1/1999 | Wang et al. |
| 6,005,199 A | 12/1999 | Harada et al. |
| 6,197,017 B1 | 3/2001 | Brock et al. |
| 6,331,181 B1 | 12/2001 | Tierney et al. |
| 6,371,952 B1 | 4/2002 | Madhani et al. |
| 6,394,998 B1 | 5/2002 | Wallace et al. |
| 6,459,926 B1 | 10/2002 | Nowlin et al. |
| 6,494,882 B1 | 12/2002 | Lebouitz et al. |
| 6,594,552 B1 | 7/2003 | Nowlin et al. |
| 6,723,106 B1* | 4/2004 | Charles .................. B25J 9/1065 606/130 |
| 6,730,021 B2 | 5/2004 | Vassiliades, Jr. et al. |
| 6,817,974 B2 | 11/2004 | Cooper et al. |
| 6,991,627 B2 | 1/2006 | Madhani et al. |
| 6,994,708 B2 | 2/2006 | Manzo |
| 7,083,571 B2 | 8/2006 | Wang et al. |
| 7,169,141 B2* | 1/2007 | Brock ................ A61B 17/0644 606/1 |
| 7,331,967 B2 | 2/2008 | Lee et al. |
| 7,935,130 B2 | 5/2011 | Williams |
| 8,256,306 B1 | 9/2012 | Bauer et al. |
| 8,306,656 B1 | 11/2012 | Schaible et al. |
| 8,444,631 B2 | 5/2013 | Yeung et al. |
| 8,479,969 B2 | 7/2013 | Shelton, IV |
| 8,506,555 B2 | 8/2013 | Ruiz Morales |
| 8,551,115 B2 | 10/2013 | Steger et al. |
| 8,597,280 B2 | 12/2013 | Cooper et al. |
| 8,602,288 B2 | 12/2013 | Shelton, IV et al. |
| 8,603,077 B2 | 12/2013 | Cooper et al. |
| 8,620,473 B2 | 12/2013 | Diolaiti et al. |
| 8,628,518 B2 | 1/2014 | Blumenkranz et al. |
| 8,771,270 B2 | 7/2014 | Burbank |
| 8,800,838 B2 | 8/2014 | Shelton, IV |
| 8,808,166 B2 | 8/2014 | Hosaka |
| 8,840,628 B2* | 9/2014 | Green .................... A61B 34/71 606/1 |
| 8,945,095 B2 | 2/2015 | Blumenkranz et al. |
| 9,028,494 B2 | 5/2015 | Shelton, IV et al. |
| 9,078,684 B2 | 7/2015 | Williams |
| 9,144,452 B2 | 9/2015 | Scott et al. |
| 9,192,448 B2 | 11/2015 | Blumenkranz |
| 9,204,923 B2 | 12/2015 | Manzo et al. |
| 9,232,979 B2 | 1/2016 | Parihar et al. |
| 9,259,274 B2 | 2/2016 | Prisco |
| 9,291,793 B2 | 3/2016 | Cooper |
| 9,707,684 B2 | 7/2017 | Ruiz et al. |
| 9,757,149 B2 | 9/2017 | Cooper et al. |
| 9,782,214 B2 | 10/2017 | Houser et al. |
| 9,918,731 B2 | 3/2018 | Cooper et al. |
| 9,931,106 B2 | 4/2018 | Au et al. |
| 9,952,107 B2 | 4/2018 | Blumenkranz et al. |
| 9,962,228 B2 | 5/2018 | Schuh et al. |
| 10,022,193 B2 | 7/2018 | Cooper et al. |
| 10,076,348 B2 | 9/2018 | Anderson et al. |
| 10,085,809 B2 | 10/2018 | Blumenkranz et al. |
| 10,130,366 B2 | 11/2018 | Shelton, IV et al. |
| 10,201,365 B2 | 2/2019 | Boudreaux et al. |
| 10,219,874 B2 | 3/2019 | Yu et al. |
| 10,238,458 B2 | 3/2019 | Verner et al. |
| 10,335,176 B2 | 7/2019 | Anderson et al. |
| 10,357,321 B2 | 7/2019 | Donlon et al. |
| 10,398,433 B2 | 9/2019 | Boudreaux et al. |
| 10,470,830 B2 | 11/2019 | Hill et al. |
| 10,550,918 B2 | 2/2020 | Cooper et al. |
| 10,653,435 B2 | 5/2020 | Shelton, IV et al. |
| 10,682,141 B2 | 6/2020 | Moore et al. |
| 10,881,280 B2 | 1/2021 | Baez, Jr. |
| 10,980,556 B2 | 4/2021 | Anderson et al. |
| 11,020,112 B2 | 6/2021 | Shelton, IV et al. |
| 11,045,270 B2 | 6/2021 | Shelton, IV et al. |
| 2003/0135203 A1 | 7/2003 | Wang et al. |
| 2007/0005002 A1 | 1/2007 | Millman et al. |
| 2007/0043338 A1 | 2/2007 | Moll et al. |
| 2007/0078484 A1 | 4/2007 | Talarico et al. |
| 2007/0119274 A1 | 5/2007 | Devengenzo et al. |
| 2007/0137371 A1 | 6/2007 | Devengenzo et al. |
| 2007/0156019 A1 | 7/2007 | Larkin et al. |
| 2008/0009838 A1 | 1/2008 | Schena et al. |
| 2008/0046122 A1 | 2/2008 | Manzo et al. |
| 2008/0065102 A1 | 3/2008 | Cooper |
| 2008/0065105 A1 | 3/2008 | Larkin et al. |
| 2008/0087871 A1 | 4/2008 | Schena et al. |
| 2008/0103491 A1 | 5/2008 | Omori et al. |
| 2008/0132893 A1 | 6/2008 | D'Amelio et al. |
| 2008/0221391 A1 | 9/2008 | Weitzner et al. |
| 2009/0088774 A1 | 4/2009 | Swarup et al. |
| 2010/0198253 A1 | 8/2010 | Jinno et al. |
| 2010/0219388 A1 | 9/2010 | Schena |
| 2010/0298844 A1* | 11/2010 | Blumenkranz ........ A61B 34/37 156/60 |
| 2010/0313679 A1 | 12/2010 | Larkin et al. |
| 2010/0318101 A1 | 12/2010 | Choi et al. |
| 2011/0015650 A1 | 1/2011 | Choi et al. |
| 2011/0071543 A1 | 3/2011 | Prisco et al. |
| 2011/0196419 A1 | 8/2011 | Cooper |
| 2011/0201883 A1 | 8/2011 | Cooper et al. |
| 2011/0277775 A1 | 11/2011 | Holop et al. |
| 2011/0282351 A1 | 11/2011 | Cooper et al. |
| 2011/0282356 A1 | 11/2011 | Solomon et al. |
| 2011/0295269 A1 | 12/2011 | Swensgard et al. |
| 2011/0295270 A1 | 12/2011 | Giordano et al. |
| 2012/0010628 A1 | 1/2012 | Cooper et al. |
| 2012/0123441 A1 | 5/2012 | Au et al. |
| 2013/0144395 A1 | 6/2013 | Stefanchik et al. |
| 2013/0291654 A1 | 11/2013 | Blumenkranz et al. |
| 2014/0005662 A1 | 1/2014 | Shelton, IV |
| 2014/0005678 A1 | 1/2014 | Shelton, IV et al. |
| 2014/0005708 A1 | 1/2014 | Shelton, IV |
| 2014/0238174 A1 | 8/2014 | Ikebe |
| 2014/0257333 A1 | 9/2014 | Blumenkranz |
| 2014/0330432 A1* | 11/2014 | Simaan .................. B25J 9/1625 700/250 |
| 2015/0150635 A1 | 6/2015 | Kilroy et al. |
| 2015/0374447 A1 | 12/2015 | Blumenkranz et al. |
| 2016/0058443 A1 | 3/2016 | Yates et al. |
| 2016/0216167 A1 | 7/2016 | Blumenkranz et al. |

(56) References Cited

U.S. PATENT DOCUMENTS

| | | |
|---|---|---|
| 2016/0296219 A1 | 10/2016 | Srivastava et al. |
| 2016/0361128 A1 | 12/2016 | Seeber et al. |
| 2017/0007345 A1 | 1/2017 | Smith et al. |
| 2017/0165017 A1 | 6/2017 | Chaplin et al. |
| 2017/0172509 A1 | 6/2017 | Hein et al. |
| 2017/0172687 A1 | 6/2017 | Smith et al. |
| 2017/0215944 A1 | 8/2017 | Keffeler |
| 2018/0042689 A1 | 2/2018 | Mozdzierz et al. |
| 2018/0078249 A1 | 3/2018 | Stoy et al. |
| 2018/0110577 A1 | 4/2018 | Lee et al. |
| 2019/0069966 A1 | 3/2019 | Petersen et al. |
| 2019/0094084 A1 | 3/2019 | Swinehart et al. |
| 2019/0125354 A1 | 5/2019 | Deck et al. |
| 2019/0175188 A1 | 6/2019 | Pv |
| 2019/0175887 A1 | 6/2019 | Shameli |
| 2019/0201018 A1 | 7/2019 | Shelton, IV et al. |
| 2019/0223960 A1 | 7/2019 | Chaplin et al. |
| 2019/0231464 A1 | 8/2019 | Wixey et al. |
| 2019/0239965 A1 | 8/2019 | Abbott |
| 2019/0249759 A1 | 8/2019 | Abbott |
| 2019/0307522 A1 | 10/2019 | Lambrecht et al. |
| 2019/0328467 A1 | 10/2019 | Waterbury et al. |
| 2019/0336228 A1 | 11/2019 | Blumenkranz et al. |
| 2020/0015876 A1* | 1/2020 | Chou ................. A61B 18/00 |
| 2020/0173525 A1 | 6/2020 | Cooper et al. |
| 2020/0278265 A1 | 9/2020 | Suresh |
| 2020/0405375 A1 | 12/2020 | Shelton, IV et al. |
| 2021/0033478 A1 | 2/2021 | Shang |
| 2021/0045819 A1 | 2/2021 | Castillo et al. |
| 2021/0045825 A1* | 2/2021 | Lee ..................... A61B 34/71 |
| 2021/0186544 A1 | 6/2021 | Anderson et al. |
| 2021/0282793 A1 | 9/2021 | Anderson et al. |
| 2021/0353352 A1 | 11/2021 | Petersen |
| 2022/0003615 A1 | 1/2022 | Kadokura |
| 2023/0003596 A1 | 1/2023 | Petersen |
| 2023/0363849 A1 | 11/2023 | Comenencia et al. |
| 2024/0090959 A1 | 3/2024 | Deyanov |
| 2024/0148405 A1 | 5/2024 | Moreira, I et al. |

FOREIGN PATENT DOCUMENTS

| | | |
|---|---|---|
| CN | 104116547 A | 10/2014 |
| CN | 105682597 A | 6/2016 |
| EP | 2362285 A2 | 8/2011 |
| EP | 2736680 A2 | 6/2014 |
| EP | 3103374 A1 | 12/2016 |
| JP | H10249777 A | 9/1998 |
| JP | 2000172355 A | 6/2000 |
| JP | 2005288590 A | 10/2005 |
| KR | 100778387 B1 | 11/2007 |
| WO | WO-8910242 A1 | 11/1989 |
| WO | WO-0030557 A1 | 6/2000 |
| WO | WO-2009123891 A1 | 10/2009 |
| WO | WO-2012068156 A2 | 5/2012 |
| WO | WO-2012166806 A1 | 12/2012 |
| WO | WO-2013118774 A1 | 8/2013 |
| WO | WO-2015069887 A1 | 5/2015 |
| WO | WO-2015142290 A1 | 9/2015 |
| WO | WO-2016161449 A1 | 10/2016 |
| WO | WO-2016172299 A1 | 10/2016 |
| WO | WO-2016189284 A1 | 12/2016 |
| WO | WO-2017064303 A1 | 4/2017 |
| WO | WO-2017188851 A1 | 11/2017 |
| WO | WO-2018049217 A1 | 3/2018 |
| WO | WO-2018069679 A1 | 4/2018 |
| WO | WO-2018075527 A1 | 4/2018 |
| WO | WO-2019099562 A1 | 5/2019 |
| WO | WO-2020102774 A1 | 5/2020 |
| WO | WO-2020102776 A1 | 5/2020 |
| WO | WO-2020102778 A1 | 5/2020 |
| WO | WO-2020102780 A1 | 5/2020 |
| WO | WO-2021055276 A1 | 3/2021 |
| WO | WO-2021076765 A1 | 4/2021 |
| WO | WO-2021219396 A1 | 11/2021 |
| WO | WO-2022056213 A1 | 3/2022 |
| WO | WO-2022132885 A1 | 6/2022 |
| WO | WO-2024178115 A1 | 8/2024 |

OTHER PUBLICATIONS

International Search Report and Written Opinion for Application No. PCT/US2019/061883, mailed Mar. 24, 2020, 19 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Office Action for CN Application No. 201980074718.6, mailed Nov. 23, 2023, 37 pages.

Office Action for Chinese Application No. CN201980074718, mailed Sep. 27, 2024, 39 pages.

* cited by examiner

DECOUPLING TOOL SHAFT FROM CABLE DRIVE LOAD

CLAIM OF PRIORITY

This application is a U.S. national stage filing under 35 U.S.C. § 371 of International Application No. PCT/US2019/061883, entitled "DECOUPLING TOOL SHAFT FROM CABLE DRIVE LOAD," filed Nov. 15, 2019, which claims the benefit of priority to U.S. Provisional Patent Application Ser. No. 62/767,885, entitled "DECOUPLING TOOL SHAFT FROM CABLE DRIVE LOAD." filed Nov. 15, 2018, each of the disclosures of which is incorporated by reference herein in its entirety.

BACKGROUND

Minimally invasive medical techniques are intended to reduce the amount of tissue that is damaged during diagnostic or surgical procedures, thereby reducing patient recovery time, discomfort, and deleterious side effects. Teleoperated surgical systems that use robot assisted technology may be used to overcome limitations of manual laparoscopic and open surgery. Advances in telepresence systems provide surgeons views inside a patient's body, an increased number of degrees of motion of surgical tools, and the ability for surgical collaboration over long distances. In manual minimally invasive surgery, surgeons feel the interaction of the tools with the patient via a long shaft, which eliminates tactile cues and masks force cues.

In teleoperation surgery systems, natural force feedback is eliminated because the surgeon no longer manipulates the tool directly. Rather, an end effector at a distal end of a long shaft is actuated by control cables that extend within the shaft. A sensor at a proximal end portion of the shaft may be used to measure clinical forces imparted to patient tissue during a medical procedure due to contact between an end effector and patient tissue.

Unfortunately, forces imparted by control cables extending within the shaft may be significantly larger than clinical forces that result from contact between an end effector and patient contact tissue. Thus, there is a need to isolate clinical forces from cable forces.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DESCRIPTION OF EMBODIMENTS

Teleoperated Surgical System

Figure 1:
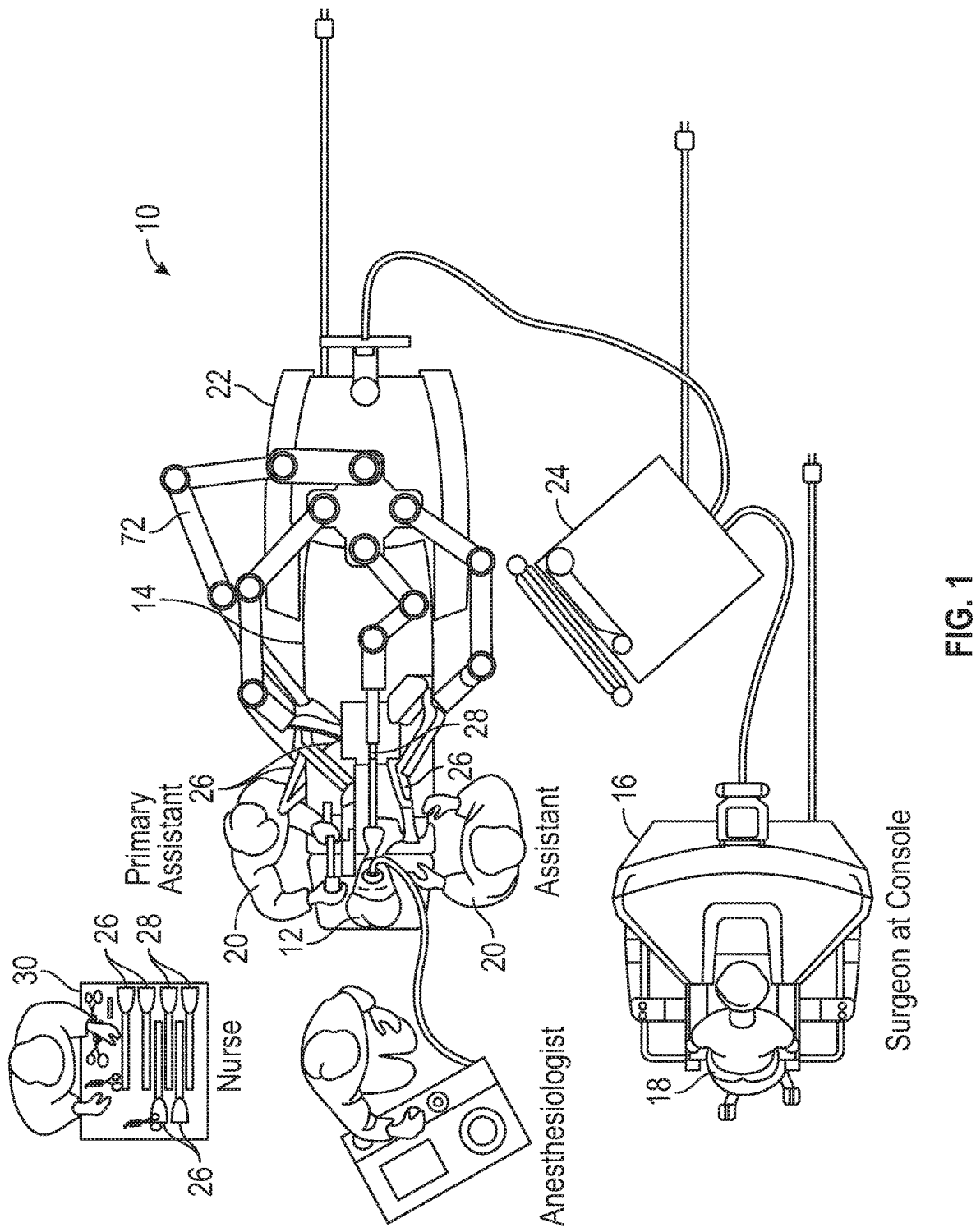
FIG. 1 is an illustrative plan view of a minimally invasive teleoperated surgical system for performing a minimally invasive diagnostic or surgical procedure on a patient who is lying on an operating table.

FIG. 1 is an illustrative plan view of a minimally invasive teleoperated surgical system 10 for performing a minimally invasive diagnostic or therapeutic surgical procedure on a patient 12 who is lying on an operating table 14. The system includes a user control unit 16 for use by a surgeon 18 during the procedure. One or more assistants 20 also may participate in the procedure. The minimally invasive teleoperated surgical system 10 further includes one or more manipulator units 22 and an auxiliary unit 24. The manipulator units 22 can manipulate at least one surgical instrument 26 through a minimally invasive incision in the body or a natural body orifice of the patient 12 while the surgeon 18 views the surgical site through the user console 16. An image of the surgical site can be obtained by an endoscope 28, such as a stereoscopic endoscope, which may be positioned using a manipulator unit 22. Computer processors located on the auxiliary unit 24 may be used to process the images of the surgical site for subsequent display to the surgeon 18 through the user console 16. The computer processor can include a logic unit and a memory that stores instructions carried out by the logic unit. In some embodiments, stereoscopic images may be captured, which allow the perception of depth during a surgical procedure. The number of surgical instruments 26 used at one time will generally depend on the diagnostic or therapeutic procedure and the space constraints within the operative site, among other factors. If it is necessary to change one or more of the surgical instruments 26 being used during a procedure, an assistant 20 may remove the surgical instrument 26 from a manipulator unit 22 and replace it with another surgical instrument 26 from a tray 30 in the operating room. An example computer processor at the auxiliary unit 24 can be configured process signals indicative of forces imparted at the surgical instrument. An example computer processor can produce haptic feedback corresponding to these imparted forces at the surgeon's console 16.

Figure 2:
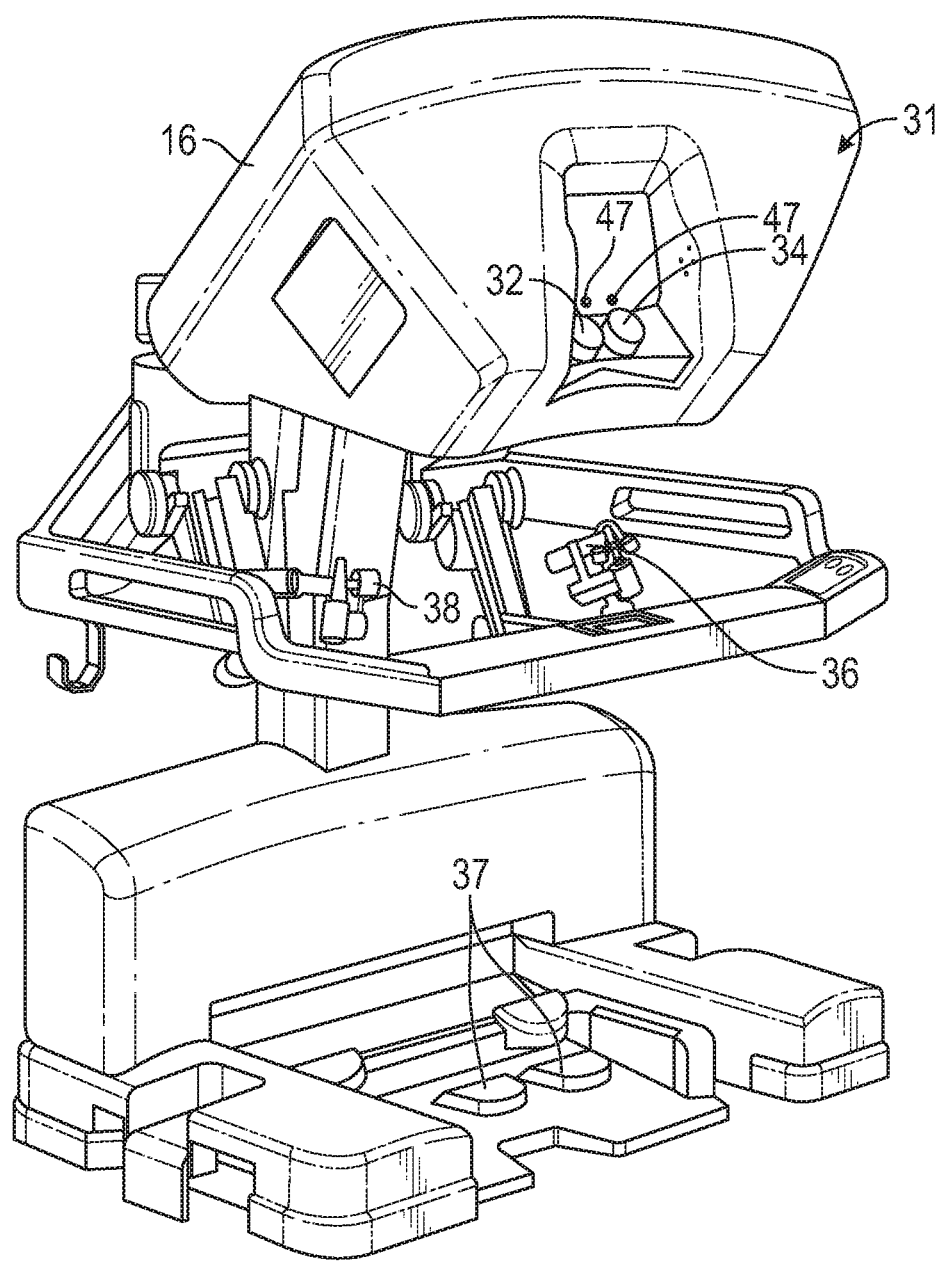
FIG. 2 is a perspective view of a surgeon's console.

FIG. 2 is a perspective view of the user console 16. The surgeon's console 16 includes a viewer display 31 that includes a left eye display 32 and a right eye display 34 for presenting the surgeon 18 with a coordinated stereoscopic view of the surgical site that enables depth perception. The user console 16 further includes one or more hand-operated control input devices 36, 38 to receive larger-scale hand control movements. One or more slave surgical instruments 26 installed for use at on one or more corresponding manipulator units 22 move in relatively smaller-scale distances that match a surgeon 18's larger-scale manipulation of the one or more master control inputs 36, 38. The master control input devices 36, 38 may provide the same mechanical degrees of freedom as their associated surgical instruments 26 to provide the surgeon 18 with telepresence, or the perception that the master control input devices 36 are integral with the slave surgical instruments 26 so that the surgeon has a keen sense of directly controlling the instruments 26. To this end, position, force, and tactile feedback sensors (not shown) may be employed to transmit position, force, and tactile sensations from the surgical instruments 26 through the control input devices 36,38 to the surgeon's hands, subject to communication delay constraints. Signals (optionally optical or electronic) modulated based upon forces detected at force sensors (not shown) at the instrument 26 may be processed by the processors at the auxiliary unit cart 24 to produce haptic feedback at the control input devices 36 that is indicative of the detected forces.

Figure 3:
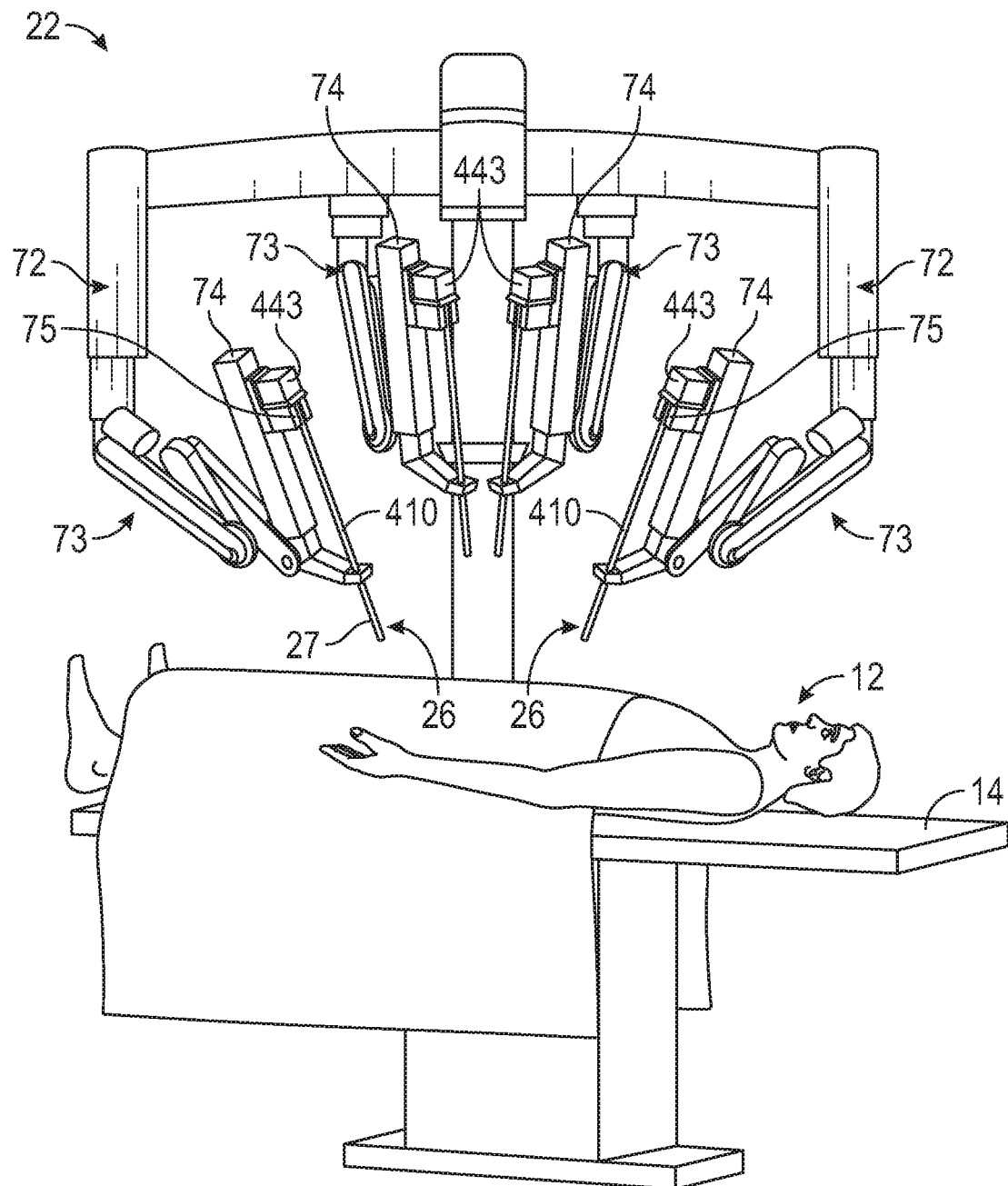
FIG. 3 is a perspective view of a manipulator unit of a minimally invasive teleoperated surgical system.

FIG. 3 is a perspective view of a manipulator unit 22 of the example minimally invasive teleoperated surgical system 10, in accordance with some embodiments. The manipulator unit 22 includes four manipulator support structures 72. Each manipulator support structure 72 includes articulated support structures 73 that are pivotally mounted end-to-end and a pivotally mounted support spar 74. A respective surgical instrument carriage 75, which includes motors to control instrument motion, is mounted at each support spar 74. Additionally, each manipulator support structure 72 can optionally include one or more setup joints (e.g., unpowered and/or lockable) at the junctions of the articulated support structures 73 and at a junction with a spar 74. A carriage 75 can be moved along a spar 74 to position the carriage 75 at different locations along the spar 74. Thus, the spars 74 can be used to position the attached to surgical instrument carriage 75 in relation to a patient 12 for surgery. Each surgical instrument 26 is detachably connected to a carriage 75. While the manipulator unit 22 is shown as including four manipulator support structures 72, more or fewer manipulator support structures 72 can be used. In general, at least one of the surgical instruments will include a vision system that typically includes an endoscopic camera instrument for capturing video images and one or more video displays for displaying the captured video images that are coupled to one of the carriages 75.

In one aspect, a carriage 75 houses multiple teleoperated actuators such as motors (not shown) that impart motion to a tension member, such as a cable drive elements, that include one or more of drive shafts and capstans (not shown), that in turn, drive cable motions that the surgical instrument 26 translates into a variety of movements of an end effector portion of the surgical instrument 26. In some embodiments, the teleoperated actuators in a carriage 75 impart motion to individual components of the surgical instrument 26 such as end effector wrist movement or jaw movement, for example.

A surgeon manipulates the master control input devices 36, 38 to control an instrument end effector. An input provided by a surgeon or other medical person to a control input device 36 or 38 (a "master" command) is translated into a corresponding action by the surgical instrument 26 (a corresponding "slave" response) through actuation of one or more remote motors. A flexible wire cable-based force transmission mechanism or the like is used to transfer the motions of each of the remotely located teleoperated motors to a corresponding instrument-interfacing actuator output located at an instrument carriage 75. In some embodiments, a mechanical adapter interface 76 mechanically couples an instrument 26 to actuators 443 within an instrument carriage to control motions inside the instrument 26. The surgical instrument 26 may be mechanically coupled to a first actuator (not shown), which may control a first motion of the surgical instrument such as longitudinal (z-axis) rotation. The surgical instrument 26 may be mechanically coupled to a second actuator (not shown), which may control second motion of the surgical instrument such as planar two-dimensional (x, y) motion. The surgical instrument 26 may be mechanically coupled to a third actuator, which may control third motion of the surgical instrument such as opening and closing of jaws of an end effector, for example.

Figure 4:
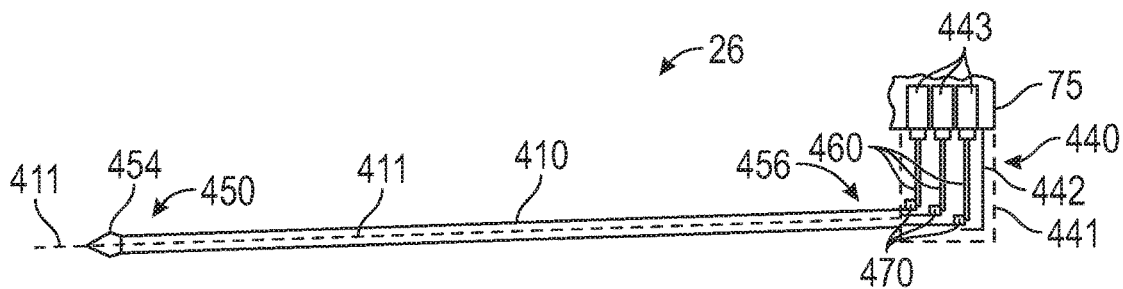
FIG. 4 is a diagrammatic side view of a surgical tool coupled to a tool carriage.

FIG. 4 is a diagrammatic side view of a surgical tool 26, coupled to a carriage 75. The tool 26 includes an elongated hollow cylindrical tubular shaft 410 having a distal end portion 450 that includes an end effector 454 for insertion into a patient's body cavity and a proximal end portion 456 that is secured to a proximal tool controller 440. An inner wall of the shaft defines a cylindrical hollow bore. The shaft 410 includes a longitudinal center axis 411 between the proximal and distal portions (a "shaft center axis"). As used herein the term "proximal" indicates a location at a surgical tool closer to a manipulator arm, and the term "distal'" indicates a location at a surgical tool more distant from the manipulator arm. The proximal tool controller 440 includes a housing 441 (shown transparent, indicated with dashed lines) that encloses a backend chassis 442 that mounts multiple cable drive elements 460, which for example may include one or more capstans and drive shafts that are configured to couple drive forces imparted by one or more actuators 443 within carriage 75 to cables extending within the shaft 410 in parallel alignment with the shaft axis 411. U.S. provisional patent application No. 62/767,895, filed on Nov. 15, 2018, which is expressly incorporated into this disclosure in its entirety, discloses drive members 460 in accordance with some embodiments. The cables 470 extend within the shaft between the drive members 460 and an end effector 454.

The end effector 454 can include a functional mechanical degree of freedom, such as jaws that open or close, or a knife that translates along a path or a wrist 452 that may move in x and y directions. U.S. Pat. No. 6,394,998 shows examples of end effectors with multiple degrees of mechanical freedom. The distal portion 450 of the tool 26 can provide any of a variety of different kinds of end effectors 454, such as the forceps, a needle driver, a cautery device, a cutting tool, an imaging device (e.g., an endoscope or ultrasound probe), or the like.

The cables 470 are operatively coupled so that movement of the cables may impart motion to end effector 454 such as to open or close of jaws, drive wrist motion, or operate other distal end effector components, for example. Thus, actuators 443 (such as motors) located at the carriage 75 near the proximal end portion 456 of the shaft 410 control movement of the end effector 454 at the distal end portion 450 of the shaft 410 by causing drive members 460 within the housing 441 of the proximal tool controller 440 to exert control forces upon cables 470 extending within the shaft 410 parallel to the shaft axis 411 between the drive members 460 and the end effector 454.

Decoupling Vertical Clinical Force from Lateral Cable Actuation Force

Figure 5A:
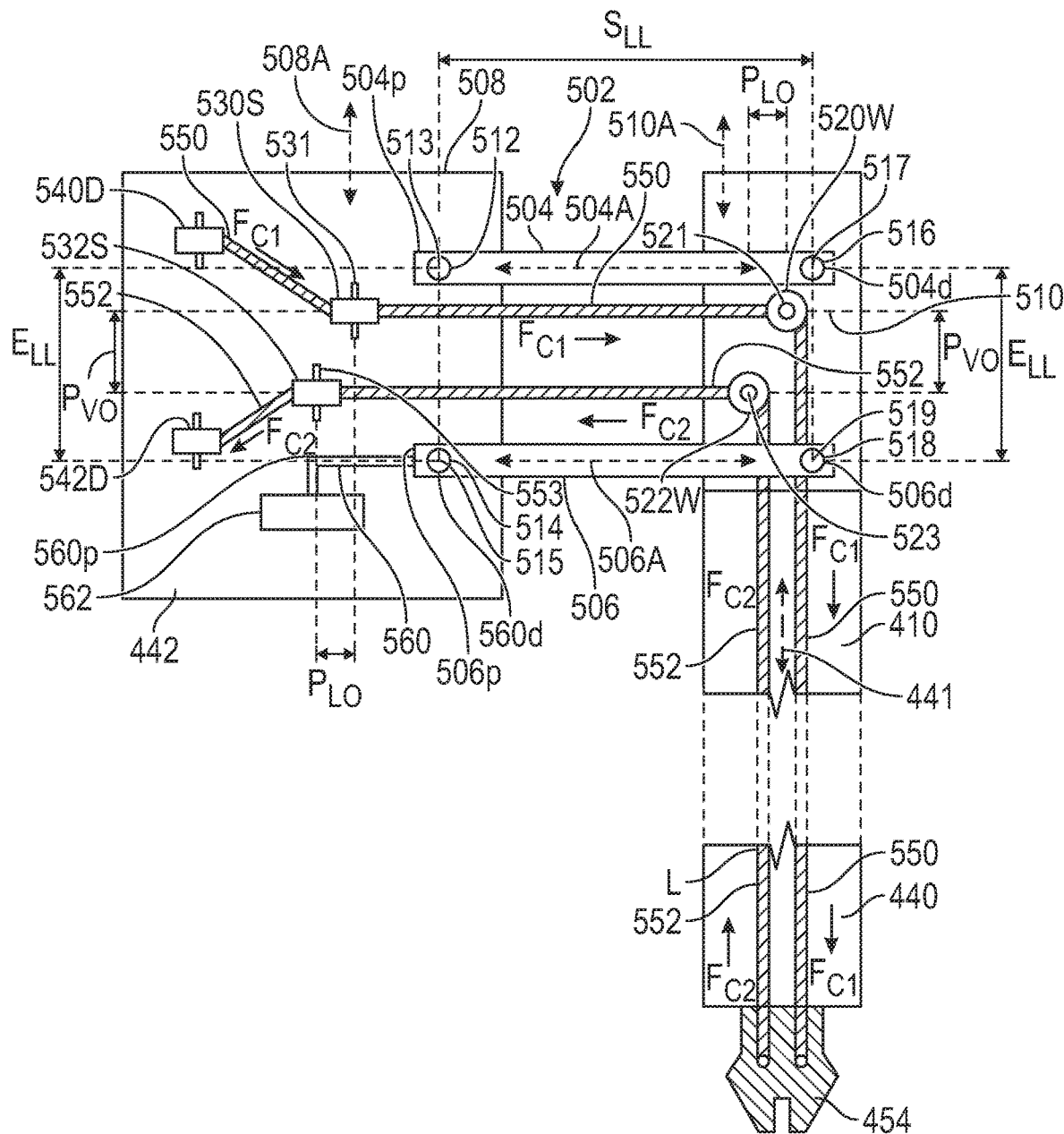
FIGS. 5A-5B are illustrative schematic diagrams representing a four-bar linkage operatively coupled to a proximal portion of a tool shaft and to a vertical sensor in a neutral position (FIG. 5A) with no vertical force imparted to the shaft and in an axially displaced position (FIG. 5B) with a vertical force imparted to the shaft.
Figure 5B:
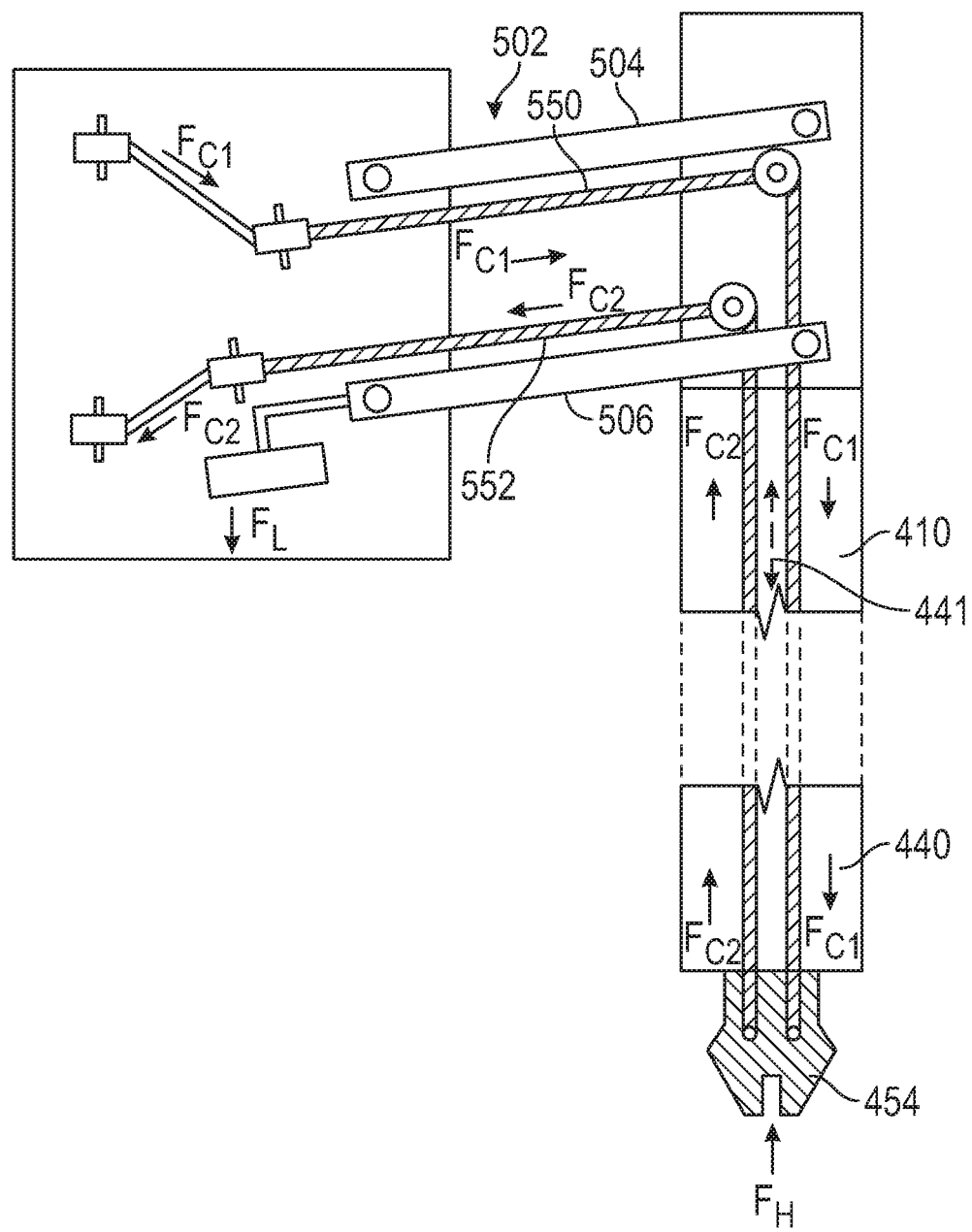

FIGS. 5A-5B are illustrative schematic diagrams representing a four-bar linkage 502 operatively coupled to a proximal portion of a carriage 75 and to a sensor 562. As shown in FIG. 5A, linkage 502 is in a neutral position with no axial force imparted to the shaft 410. As shown in FIG. 5B, linkage 502 is displaced because shaft 410 is in an axially displaced position with an axial force $F_H$ imparted to end effector 454. It can be seen that the axial force $F_H$ transmitted via shaft 410 and via linkage 502 to sensor 562, which is coupled to chassis 442. In this way axially-oriented force on end effector 454 is sensed by sensor 562.

The sensor 562 can be configured as a deflection sensor to measure an amount of deflection of a diaphragm region 702 (described below) of the sensor 562 due to the axial force $F_H$. The amount of deflection is indicative of magnitude of the force $F_H$. In some embodiments, the sensor 562 includes a force sensor configured to sense force bounded as approximately ±20 N. With no axial force imparted to the housing 440 as shown in FIG. 5A, actuators 443 within the carriage 75 impart forces to cables 550, 552 to maintain the links of the four-bar linkage 502 are in neutral positions so that no force is imparted to the sensor 562. With an axial force $F_H$ imparted to the end effector 454 as shown in FIG. 5B, links of the four-bar linkage are displaced to impart a linkage force $F_L$ to the sensor 562. In some embodiments, the linkage force $F_L$ is proportional in magnitude to a magnitude of the housing force $F_H$.

More specifically, the four-bar linkage 502 includes an upper first side link 504, a lower second side link 506, an end third frame link 508, and an end fourth coupler link 510 that are all coupled together in a double-rocker configuration. A portion of tool carriage 75, or optionally another component coupled to carriage 75, may form frame link 508. And, a portion of shaft 410, or optionally another component coupled to shaft 410, may form coupler link 510. In some embodiments, the four-bar linkage 502 is formed of a rigid material such as plastic, aluminum, titanium, stainless steel, or composites such as carbon filled plastic. A first pivot joint 512 having a first pivot joint axis 513 pivotally couples a proximal first end portion 504p of the first side link 504 to a proximal portion of the frame link 508. A second pivot joint 514 having a second pivot joint axis 515 pivotally couples a proximal first end portion 506p of the second side link 506 to a distal portion of the frame link 508. A third pivot joint 516 having a third pivot joint axis 517 pivotally couples a distal second end portion 504d of the first side link 504 to a proximal portion of the coupler link 510. A fourth pivot joint 518 having a fourth pivot joint axis 519 pivotally couples a distal second end portion 506d of the second side link 506 to a distal portion of the coupler link 510. The frame link has a fixed position in space with reference to the first, second, and fourth links, which move with reference to the frame link as shaft 410 translates laterally along shaft center axis 411. The first, second, third, and fourth pivot axes are parallel to each other.

A first side link length (the "side lateral length" or "$S_{LL}$") of the first side link 504 between the first pivot joint axis 513 and the third pivot joint axis 517 equals a second side link length of the second side link 506 between the second pivot joint axis 515 and the fourth pivot joint axis 519. In other words, the first and second side links 504, 506 have matching side lateral lengths between their respective pivot joints. The first and second side links 504, 506 each have a respective longitudinal axis 504A, 506A. The respective longitudinal axis 504A, 506A are askew from the shaft axis 411 in that they are not aligned parallel with the shaft axis 411. An end lateral length ("$E_{LL}$") of the frame link 508 between the first pivot joint axis 513 and the second pivot joint axis 515 equals an end lateral length of the coupler link 510 between the third pivot joint axis 517 and the fourth pivot joint axis 519. The frame and coupler links 508, 510 each have a respective longitudinal axis 508A, 510A. As used herein, the term lateral refers to directions parallel to longitudinal axes 504A, 506A of the first and second side links 504, 506, and the term vertical refers to directions parallel to the longitudinal axes 508A, 510A of the frame link and the coupler links 508, 510.

A proximal end portion of a hollow shaft 410 is secured at a distal portion of the coupler link 510. Thus, axial movement, vertically up and down, of the hollow shaft 410 parallel to the shaft axis 411 causes rotational motion of the four links 504, 506, 508, 510 of the four-bar linkage 502 about the four pivot joints 512, 514, 516, 518, which results in rocking motions of the of the first and second side links 504, 506. More particularly, motion imparted to the coupler link 510 by axial movement of the shaft 410 causes the first and third pivot joints 512, 516 to direct corresponding motion of the distal second end portion 504d of the first side link 504 to follow the axial motion of the shaft 440. Likewise, motion imparted to the coupler link 510 by axial movement of the shaft 440 causes the second and fourth pivot 514, 518 joints to direct corresponding motion of the distal second end portion 506d of the second side link 506 to follow the axial motion of the shaft 440. Throughout such motion of the coupler link 510 and the corresponding rocking movement of the first and second side links 504, 506, the longitudinal axes 504A, 506A of the first and second side links 504, 506 continuously extend parallel to each other, and the longitudinal axes 508A, 510A of the frame link 508 and the coupler link 510 continuously extend parallel to each other.

First and second sets of distal waterfall guide pulleys 520W, 522W are rotatably mounted to the coupler link 510. Corresponding first and second sets of proximal backend steering guide pulleys 530S, 532S are rotatably mounted to the frame link 508. In an example four-bar linkage assembly 502, the waterfall guide pulleys 520W, 522W and the steering pulleys 530S 532S are arranged to rotate perpendicular to one another. Each waterfall pulley 520W, 522W has a waterfall pulley rotation axis 521, 523 that extends parallel to the axes of the four-bar linkage pivot joints. Each steering guide pulley 530S 532S has a steering guide pulley rotation axis 531, 533 that extends perpendicular to the waterfall pulley axes and parallel to axis 508A of the 508 frame. Corresponding first and second sets of cable drive members 540D, 542D are rotatably mounted to the frame link 508 with respective rotation axes 541, 543 that extend perpendicular to the waterfall pulley axes 521, 523. It will be understood that once the cables depart the four-bar linkage, they can be driven in different directions (not shown) using other actuators. To simplify the drawings and the explanation, only one waterfall guide pulley, one steering guide pulley, and one drive member of each set is shown. It will be appreciated that the term "waterfall" is used for convenience in denoting location of the distal guide pulleys located at the coupler link 510 and how the cables are routed around the distal guide pulleys and into the shaft. Moreover, it will be appreciated that the term "steering" is used for convenience in denoting location of the proximal guide pulleys located at the frame link 508, and cables over these proximal guide pulleys can be used for end effector actuation as described above.

As shown, center axes of rotation 521, 523 of the first and second sets of waterfall guide pulleys 520W, 522W are at the coupler link 510 between the third and fourth pivot joints 516, 518. Center axes of rotation 521, 523 of the first and second sets of waterfall pulleys 520W, 522W are vertically offset from one another by a pulley vertical offset amount $P_{VO}$. The center axes 521 of the first set of waterfall pulleys 520W are vertically closer to the first side linkage 504 than are the center axes 523 of the second set of waterfall pulleys 522W. Likewise, the center axes 523 of the second set of waterfall pulleys 522W are vertically closer to the second side linkage 506 than are the center axes 521 of the first set of waterfall pulleys 520W.

Also as shown, center axes of rotation 521, 523 of the first and second sets of waterfall pulleys 520W, 522W are laterally offset from one another by a pulley lateral offset amount $P_{LO}$. This offset amount $P_{LO}$ also represents that the center axes of rotation 521 of the first set of waterfall pulleys 520W are laterally farther from the center axes 513, 515 of the first and second pivot joints 512, 514 than are the center axes of rotation 523 of the second set of waterfall pulleys 522W. The center axes 523 of the second set of waterfall pulleys 522W are disposed laterally closer to the center axes 513, 515 of the first and second pivot joints 512, 514 than are the center axes 521 of the first set of waterfall pulleys 520, by the pulley lateral offset amount $P_{LO}$. It will be appreciated that the offset amount $P_{LO}$ of cables guided about the first and second sets of waterfall pulleys 520W, 522W permits cables 550, 552 guided by these pulleys across to be positioned to extend within the shaft 410, laterally spaced apart from one another, parallel to the shaft center axis 411.

The first and second sets of backend steering guide pulleys 530S, 532S are mounted to the frame link 508 at locations vertically offset from one another by the pulley vertical offset amount $P_{VO}$. The center axes 531 of the first set of steering pulleys 530S are the frame link 508 vertically closer to the first side linkage 504 than are the center axes 533 of the second set of steering pulleys 532S. The center axes 533 of the second set of steering pulleys 532S are disposed at the frame link 508 vertically closer to the second side linkage 506 than are the center axes 531 of the first set of steering pulleys 530S. Center axes 531, 533 of the first and second sets of steering pulleys 530S, 532S are laterally offset from one another at the frame link 508 by the pulley lateral offset amount $P_{LO}$. The center axes 531 of the first set of steering pulleys 530S are disposed laterally closer to the center axes 517, 519 of the third and fourth pivot joints 516, 518 than are the center axes 533 of the second set of steering pulleys 532S. The center axes 533 of the second set of steering pulleys 532S are disposed laterally farther from the center axes 517, 519 third and fourth pivot joints 516, 518 than are the center axes 531 of the first set of steering pulleys 530S.

Multiple cables 550, 552 extend within the hollow shaft 410 parallel to the shaft axis 411. Each of the cables 550, 552 is anchored at a proximal end to a corresponding cable drive member 540D, 542D and is anchored at a distal end to the end effector 454. Each of the cables 550, 552 engages a corresponding steering pulley 530S, 532S and a corresponding waterfall pulley 520W, 522W. In some embodiments, the cables are formed of a material such as stainless steel, titanium, or tungsten, or synthetic materials such as polyethylene, or polybenzoxazole (PBO), for example. More particularly, each cable 550S, 552S includes a cable portion that wraps about a perimeter engagement surface of its associated steering pulley 530S, 532S, and each cable wraps about a perimeter engagement surfaces of its associated waterfall pulley 520W, 522W at the coupling link 510. Thus, each respective cable 550S, 552S extends between the corresponding axes 531, 533 of the cable's associated steering pulley 530S, 532S and corresponding axes 521, 523 of the cable's associated waterfall pulley 520W, 522W. To simplify the drawings and the explanation, only two cables 550, 552 are shown, although in some embodiments, four, or more than six cables may be used.

The first and second sets of waterfall pulleys 520W, 522W and the first and second sets of steering pulleys 530S, 532S are configured to maintain each of the multiple cables 550, 552 aligned parallel to the first and second side links 504, 506 both when the four-bar linkage is at rest in the neutral position and when the four-bar linkage is displaced in its rocking motion. In accordance with some embodiments, the first and second cables 550, 552 are pre-tensioned with a force of 0.5-5 lbf. An intermediate cable segment of the first cable 550 has a length between the center axes 521 of the first set of waterfall pulleys 520W and the center axes 531 of the first set of steering pulleys 530S that matches the side lateral length. Likewise, an intermediate cable segment of the second cable 552 has a length between the center axes 523 of the second set of waterfall pulleys 522W and the center axes 533 of the second set of steering pulleys 532S that matches the side lateral length. The first and second sets of steering pulleys 530S, 532S are rotatably mounted at locations at the frame link 508 and the first and second sets of waterfall pulleys 520W, 522W are rotatably mounted at locations at the coupling link 510 so that these steering pulleys and waterfall pulleys guide the intermediate cable segments of the first and second cables 550, 552 to extend parallel to the first and second side links 504, 506 while the four-bar linkage 502 is at rest and while the 4-bar linkage 502 experiences the rocking motion as shaft 410 moves vertically. Thus, even during rocking of the first and second side links 504, 506 in response to vertical motion of the shaft 440, for example, the intermediate cable segments of the first and second cables 550, 552 continuously extend parallel to the first and second side links 504, 506.

A flexure beam 560 includes a distal first end portion 560d and a proximal second end portion 560p. The distal first end portion 560d of the flexure beam is coupled to the proximal first end portion 506p of the second side link 506. The proximal second end portion 560p of the flexure beam is operatively coupled to the sensor 562. More particularly, the flexure beam 560 is operatively coupled to impart the link force $F_L$ force to the sensor 562 that that has a magnitude proportional to the axial force $F_H$ imparted by the shaft housing 440 to the coupler link 510 during axial motion of the shaft 440. In particular, for example, $F_H$ and its associated vertical displacement is transmitted from the end effector via the shaft to the coupler link. The magnitude of the link force imparted to the sensor 562 due to a corresponding force imparted by the shaft to the coupler link 510 is determined based upon the length of the flexure beam 560. Rotation of the distal first end portion 506d of the second side link 506 about the second pivot joint axis 515 during rocking motion of the four-bar linkage 502, caused by a force imparted to the coupler link 510 due to axial motion of the shaft 440, causes corresponding motion of the flexure beam 560, which in turn, imparts a corresponding link force $F_L$ to the sensor, which is proportional to the axial force $F_H$ imparted by the shaft 440 to the coupler link 410.

In some embodiments, the flexure, beam 560 is optionally formed of a material such as aluminum, stainless steel, or titanium, or it may optionally be formed of a composite material such as carbon filled plastic. Flexure beam 560 is configured to have a bending stiffness in a direction parallel to the shaft center axis 411 of the shaft 410 that is less than a bending stiffness of the linkages of the four-bar linkage 502. The linkages of the four-bar linkage 502 have a high enough bending stiffness such that they do not bend in response to cable forces exerted by the cable drive members 540D, 542D. Likewise, the links of the four-bar linkage 502 have a high enough bending stiffness such that they do not bend during normal rocking motion m response to axial motion of the shaft 410. The instrument shaft 410 has an insertion stiffness in a range of 5-50 N/mm. In some embodiments, total cable forces may be in a range of about 100 lbf. By comparison, a bending stiffness of the flexure beam 560 is small enough to flex during normal rocking motion of the four-bar linkage 502 in response to axial motion of the shaft 410. More particularly, in some embodiments, the flexure beam 560 has a bending stiffness that is low enough to flexibly bend, without sustaining damage such as breakage, in response to certain shaft forces imparted to the coupler link 510 during axial motion of the shaft 410. In some embodiments, the shaft force is caused by axial clinical force imparted to an end effector 454 at a distal end portion of the shaft 410 due to the end effector contacting anatomical tissue, for example. In some embodiments, such clinical forces may be in a range of about 20 N.

The configuring of the waterfall pulleys 520W, 522W and the steering pulleys 530S, 532S to maintain the intermediate cable segments in parallel alignment with the longitudinal axes 504A, 506A of the first and second side linkages 504, 506 at all times, including throughout rocking motion four-bar linkage 502, decouples cable forces at the four-bar linkage 502 from forces imparted at the four-bar linkage 502 due to motion of the shaft 410. The larger cable forces are imparted to the intermediate cable segments in a direction parallel to the longitudinal axis 504A, 506A of the first and second side links 504, 506. Much smaller clinical forces imparted to shaft can be imparted to the coupler linkage 510 in a direction perpendicular to the longitudinal axis 504A, 506A of the first and second side links 504, 506. Thus, cable forces $F_{C1}$, $F_{C2}$ on cables 550,552 that drive end effector 454 and that are imparted to the four-bar is linkage 502 are isolated from the axial forces $F_H$ imparted to the four-bar linkage 502 due to axial motion of the shaft 410. Therefore, a smaller contact force at an end effector 454 imparts a corresponding vertical force $F_H$ to the shaft 410 and to the coupler link 510, and this vertical force is isolated from larger lateral cable forces $F_{C1}$, $F_{C2}$ imparted to the cables 550, 552. The vertical (axial) force $F_H$ causes a rocking motion of the four-bar linkage 502 and of the flexure beam 560 coupled thereto, which in turn, imparts a link force $F_L$ force to the sensor 560 that has a magnitude proportional to the smaller vertical (axial) force $F_H$.

Figure 5C:
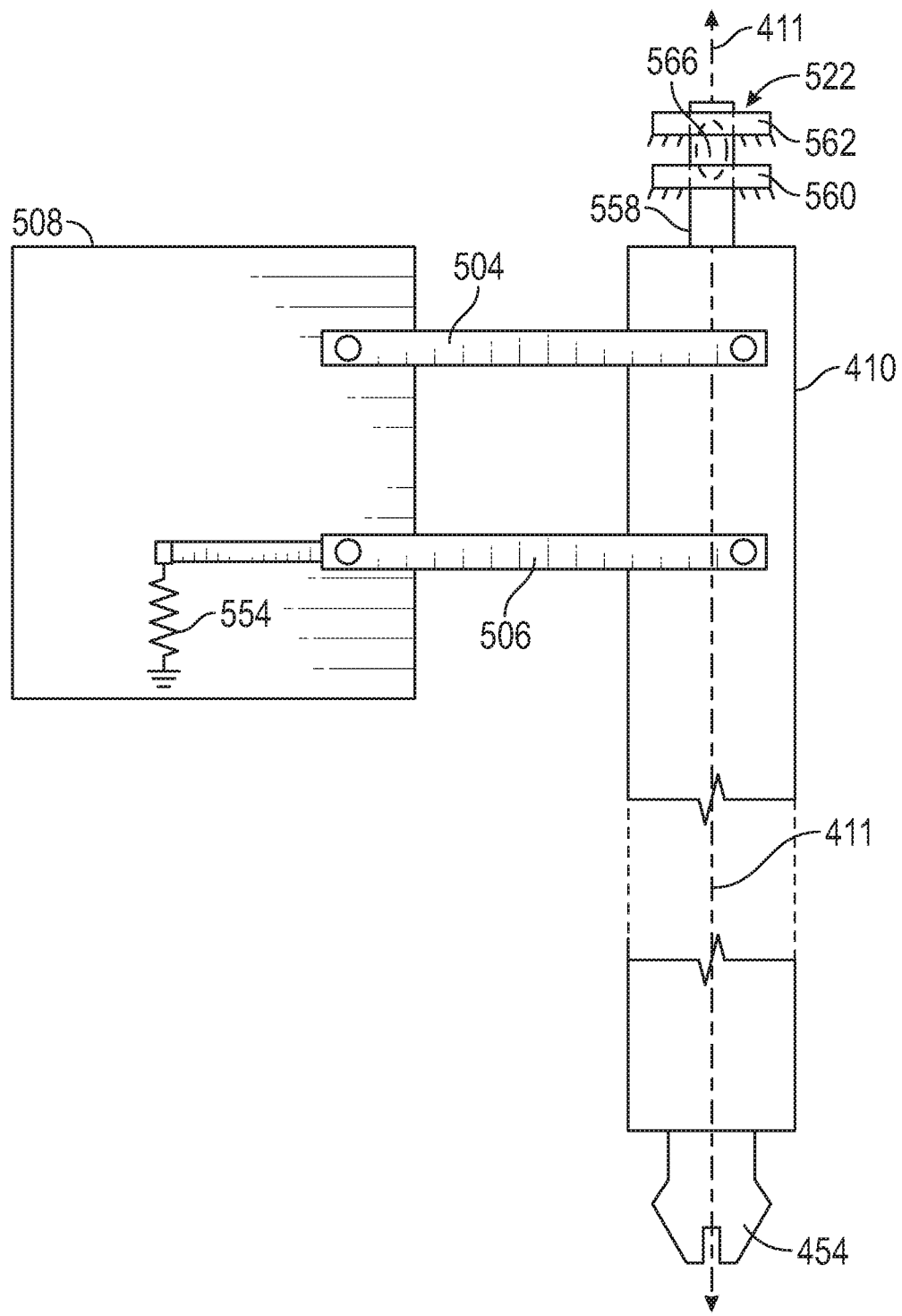
FIG. 5C is an illustrative schematic diagram showing an alternative example four-bar linkage that includes a differential coaxial inductive displacement sensor and a spring force sensor.

FIG. 5C is an illustrative schematic diagram showing an alternative example four-bar linkage that includes a differential coaxial coil inductive displacement sensor 552 and a spring force sensor 554. In various embodiments, a dual-coil distance displacement force sensor 552 can be used in conjunction flexure 554 to measure axial force upon the instrument shaft 410. The axial direction is taken as a direction parallel to the center axis 411. An example displacement sensor 552 includes a sensor shaft 558, a proximal annular coil 560, and a distal annular coil 562. The proximal and distal coils are at a fixed location and coaxially aligned with the sensor shaft 558. The sensor shaft 558 and the proximal and distal coils 560, 562 are arranged to permit the sensor shaft 558 to move axially while inserted within the coils 560, 562. A magnetic material structure 566 is located on the sensor shaft 558, which is fixed to the tool shaft 410 so that the tool shaft 410 and the sensor shaft 558 move in unison, axially. An axial direction force imparted to an end effector 454 at a distal end of the tool shaft 410 that axially displaces the tool shaft 410 results in corresponding axial force upon and displacement of the sensor shaft 558.

When 'at rest,' with no axial direction force exerted upon the tool shaft 410, the sensor shaft 558 can be axially positioned such that the magnetic material structure 566 is in part within each of the annular proximal and annular distal coils 560, 562. With no axial direction force excited upon the tool shaft 410, equal portions of the magnetic material structure 566 can be located within each of the coils 560, 562. Each coil can be coupled into a separate LC circuit (not shown) in which the coil acts as an inductor (L) and in which the inductance varies with the amount of the magnetic material contained within the respective coil. The resonant frequency of each circuit varies with changes in inductance of the respective circuit.

When an axial force causes axial movement of the tool shaft 410 and the sensor shaft 558, the proportion of the magnetic material structure 566 within each of the proximal and distal coils 560, 562 changes. The inductance of one of the coils increase while the inductance of the other decreases. As a result, the proximal and distal coils 560,562 have inductance values that do not match. The separate LC circuits are used to measure the difference in inductances of the coils, which provides an indication of axial displacement distance of the sensor shaft 558.

The flexure 554 has one portion secured to a proximal end portion of a lower second side link 506 and has an opposite end secured to the frame link 508. The flexure 554 has known stiffness that can be used to force based upon displacement of the flexure. A measure of displacement of the sensor shaft 558 based upon measurement of inductance values of the proximal and distal coils 560, 562 is used to determine sensor shaft displacement distance. The inductive coils 560, 562 can be used to measure shaft displacement. The flexure 554 can be used to measure corresponding axial force; the flexure has a known stiffness and the amount of flexure displacement is indicative of magnitude of axial force imparted the end effector and transmitted by side link 506 to the flexure 554. Thus, shaft displacement can be calibrated to flexure displacement and flexure stiffness can be used to determine axial force corresponding to shaft displacement. An example of force measurement using a differential coaxial inductive displacement sensor used with spring force sensor is provided in U.S. Patent Application No. 62/901,729, filed Sep. 17, 2019, which is expressly incorporated herein in its entirety.

Figure 6A:
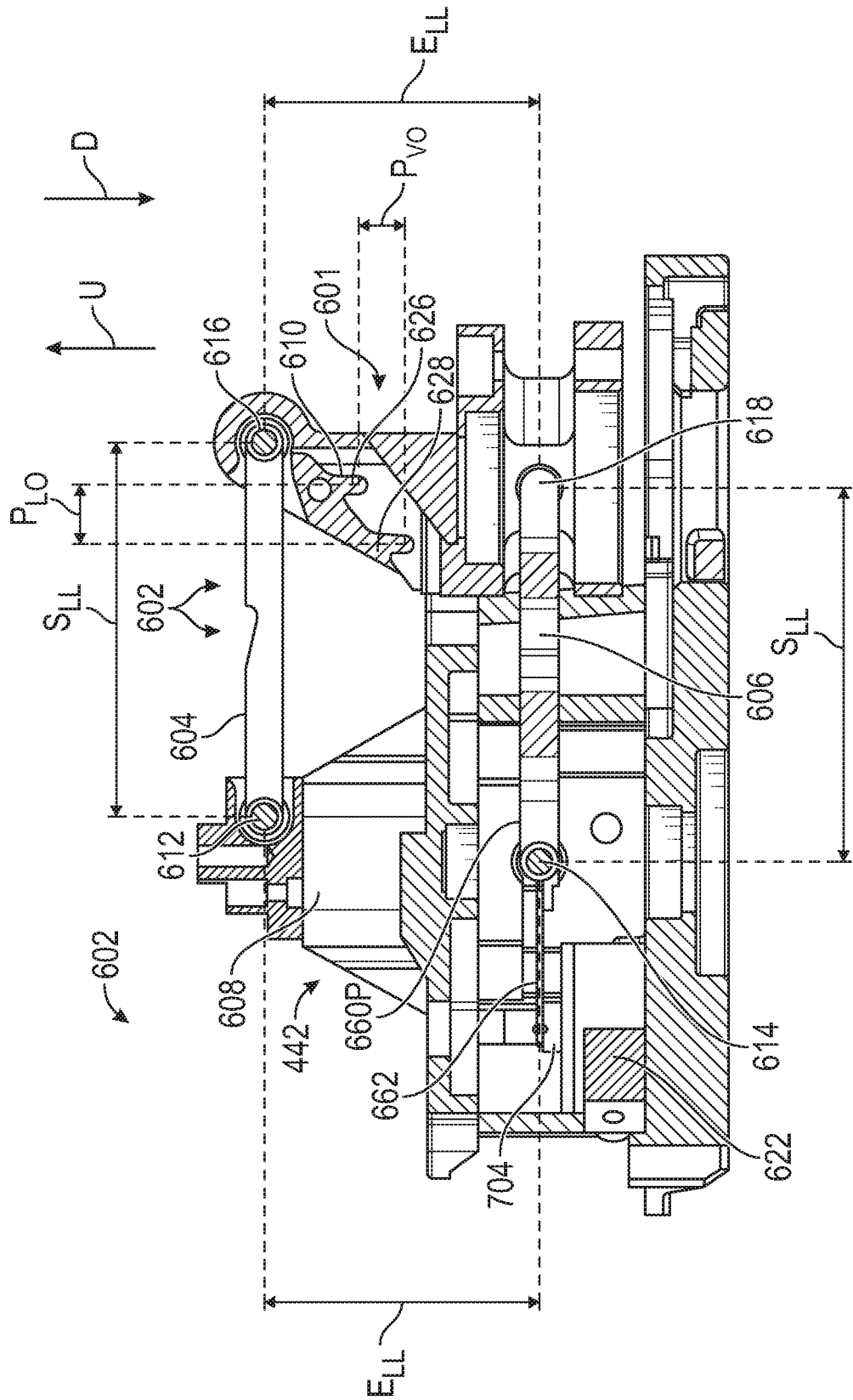
FIGS. 6A-6C are illustrative side view of an embodiment of a four-bar linkage in example neutral (FIG. 6A), lowered (FIG. 6B), and raised (FIG. 6C), in which a backend chassis and a shaft assembly are coupled to act as links.
Figure 6C:
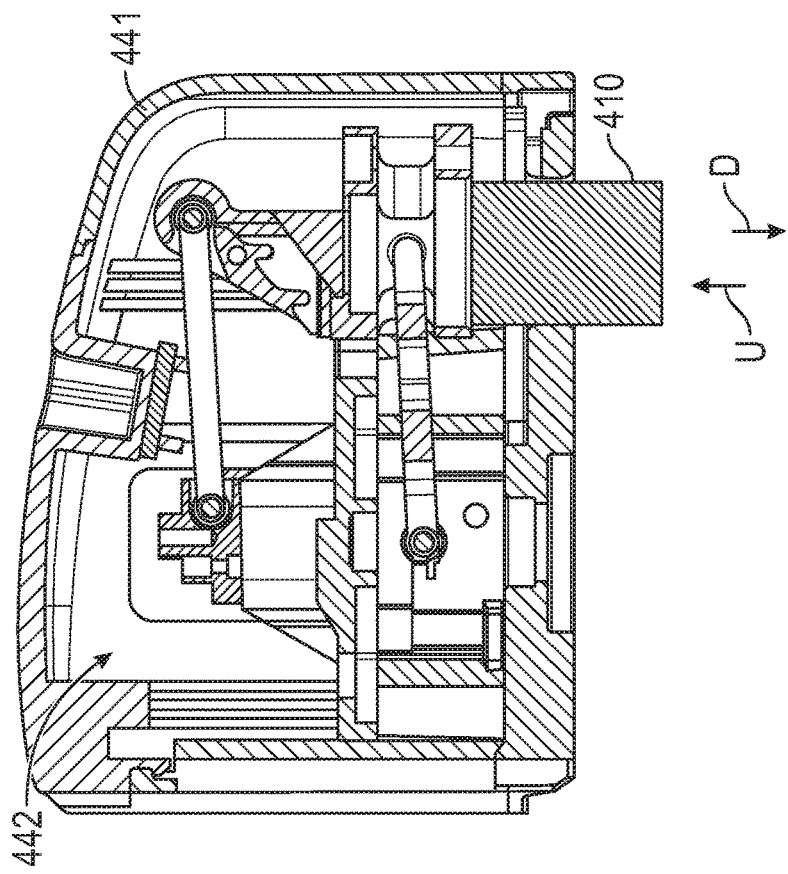
Figure 6B:
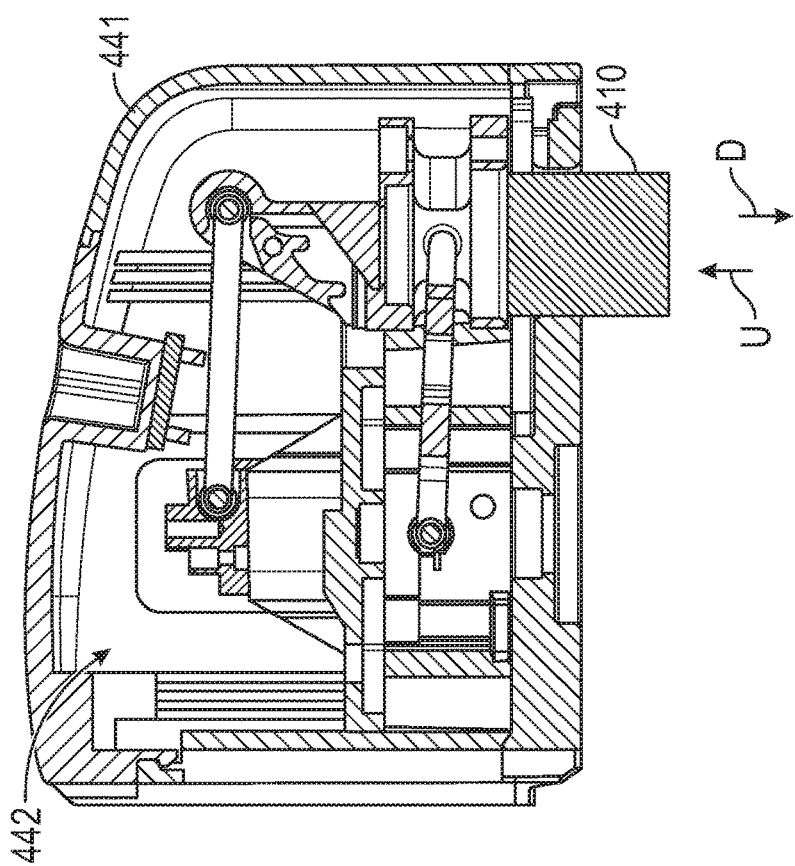

FIGS. 6A-6C are illustrative side view of an embodiment of a four-bar linkage 602 in which the backend chassis 442 and a shaft assembly 601 are coupled to act as a frame link and coupler link, respectively. As explained above, the proximal tool controller 440 includes the backend chassis 442. FIG. 6A shows the four-bar linkage 602 in a neutral position in which upper and lower sidebars 604, 606 are aligned horizontal. FIG. 6B shows the upper and lower sidebars 604, 606 rotated slightly downward when the shaft 410 is disposed in an axially lower position. FIG. 6C shows the upper and lower sidebars 604, 606 rotated slightly upward when the shaft 3s disposed in an axially vertically higher position.

The four-bar linkage includes an upper first link 604 and a lower second side link 606 frame link 608, a coupler link 610. The backend chassis 442 acts as the frame link 608. The shaft assembly 601 acts as the coupler link 610. The waterfall pulleys and steering pulleys are omitted to simplify the drawing and to avoid hiding details of the four-bar linkage 602.

A proximal end portion of the upper first side link 604 is rotatably coupled at a first pivot joint 612 to the frame link 608. A proximal end portion of the lower second side link 506 is rotatably coupled at a second pivot joint 614 to the frame link 608. A distal end portion of the upper first side link 604 is rotatably coupled at a third pivot joint 616 to the frame link 610. A distal end portion of the lower second side link 606 is rotatably coupled at a fourth pivot joint 616 to the frame link 610. A side lateral length ($S_{LL}$) along the upper first side link between the first and third pivot joints equals a side lateral length along the lower second side link between the second and fourth pivot joints. An end lateral length ($E_{LL}$) of the frame link 608 between the first and second pivot joints 612, 614 equals an end lateral length ($E_{LL}$) of the coupler link 610 between the third and fourth pivot joints 616, 618.

A first waterfall pulley mount 626 and a second waterfall pulley mount 628 are disposed at the coupler link 610 to mount first and second sets of waterfall pulleys (not shown) about first and second waterfall pulley axes that extend parallel to rotation axes of the first through fourth pivot joints 612-618. The first and second waterfall pulley mounts 626, 628 are laterally offset from one another by a pulley lateral offset amount $P_{LO}$. The first and second waterfall pulley mounts 626, 628 are vertically offset from one another by a pulley vertical offset amount $P_{VO}$.

A flexure beam 660 is fixedly secured to rotate in unison with the second side link 606 about the second pivot joint 614. More particularly, a distal end portion 660d of the flexure beam is coupled to a distal end portion of the lower second side link 606, and a proximal end portion is operatively couple to a sensor 662. Upward motion of the shaft assembly in direction of arrow "U" causes downward motion of the proximal end portion 660p of the flexure bean 660 in direction of arrow "D". To simplify the drawings, the beam flexure and sensor are not shown in FIGS. 6B-6C.

Figure 7:
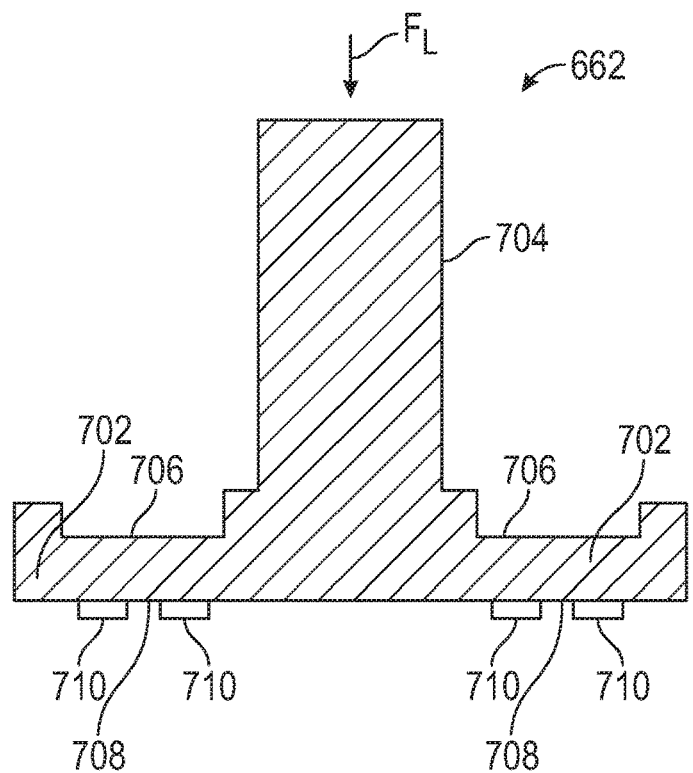
FIG. 7 is an illustrative schematic side cross-sectional view of an embodiment of a sensor of FIG. 6.

FIG. 7 is an illustrative schematic side cross-sectional view of an embodiment of the sensor 662 of FIGS. 6A-6C. In some embodiments, the sensor is a diaphragm force sensor that includes a thin annular substantially planar diaphragm 702 and upstanding sensor beam 704 disposed to impart a perpendicular force to the diaphragm 702. The diaphragm 702 includes reverse facing planar first and second surfaces 706, 708. Strain gauges 710 are disposed upon the second surface 708. The proximal end portion 660p of the flexure beam 660 is operatively coupled to impart a perpendicular link force $F_L$ to the upstanding sensor beam 704 in response to rotation of the lower second side link 606 about the second pivot joint 614. In some embodiments, the first surface 706 of the diaphragm 702 may be contoured to increase force measurement sensitivity. U.S. Patent Application No. 62/767,891, filed Nov. 15, 2018, which is expressly incorporated herein in its entirety by this reference, discloses a diaphragm sensor with a contoured diaphragm surface.

Figure 8:
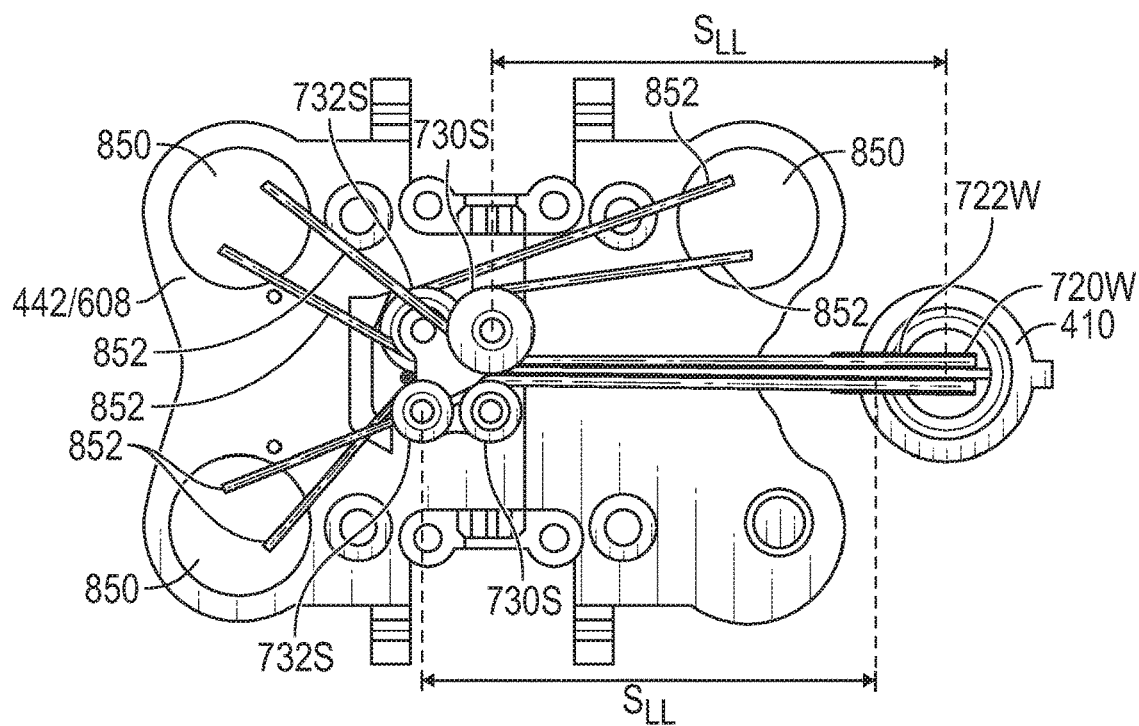
FIG. 8 is an illustrative simplified top view showing a layout of steering guide pulleys, waterfall guide pulleys and cable drive members mounted to the four-bar linkage embodiment of FIGS. 6A-6C in accordance with some embodiments.

FIG. 8 is an illustrative simplified top view showing a layout of steering guide pulleys 730S, 732S, waterfall guide pulleys 720W, 7222W and cable drive elements 850 mounted to the four-bar linkage embodiment of FIGS. 6A-6C in accordance with some embodiments. Various details are omitted or simplified to not obscure the layout of the pulleys. A first set of steering pulleys 730S and a second set of steer steering 732S are rotatably mounted to the chassis 442, which acts as the frame link 608. A first set of waterfall pulleys 720W and a second set of waterfall pulleys 722W are mounted to the shaft assembly (not shown), which acts as the coupler link 610. In some embodiments, the cable drive elements 850 may include capstans mounted to the chassis 442 act as cable drive elements 850. Rotation axes of the first and second sets of steering pulleys 730S, 732S are laterally offset from and are perpendicular to rotation axes of the first and second sets of waterfall pulleys 720W, 722W. The lateral offset between the rotation axes of the first set of steering pulleys 730S and the rotation axes of the first set of waterfall pulleys 720W is the side lateral length ($S_{LL}$) between the first and third pivot joints 612, 616. The lateral offset between the rotation axes of the second set of steering pulleys 732S and the rotation axes of the second set of waterfall pulleys 722W is the side lateral length ($S_{LL}$) between the second and fourth pivot joints 614, 618. Thus, the rotational axes offsets, $S_{LL}$, match. The illustrative first and second sets of steering pulleys 730S, 732S each have some pulleys with different diameters, although each steering pulley is offset from its corresponding set of waterfall pulleys by the side lateral length ($S_{LL}$). It will be understood that the first and second sets of waterfall pulleys 720W, 722W also each have some pulleys with different diameters. Smaller diameter steering pulleys are paired with larger diameter waterfall pulleys and vice versa so that cable lengths are the same for all steering/waterfall pulley pairs. It will be appreciated that use of pulleys having different diameters more readily permits distribution of cables 852 at different locations within the shaft 410. The different diameter pulleys also allow cables to be routed to the correct capstan while keeping the cable parallel to linkages 504 and 506. Individual cables 852 are secured to an associated capstan, are guided by individual steering pulleys and associated individual waterfall pulleys, which guide the individual cables 852 into alignment with the longitudinal axis 411 of the shaft 410.

Figure 9:
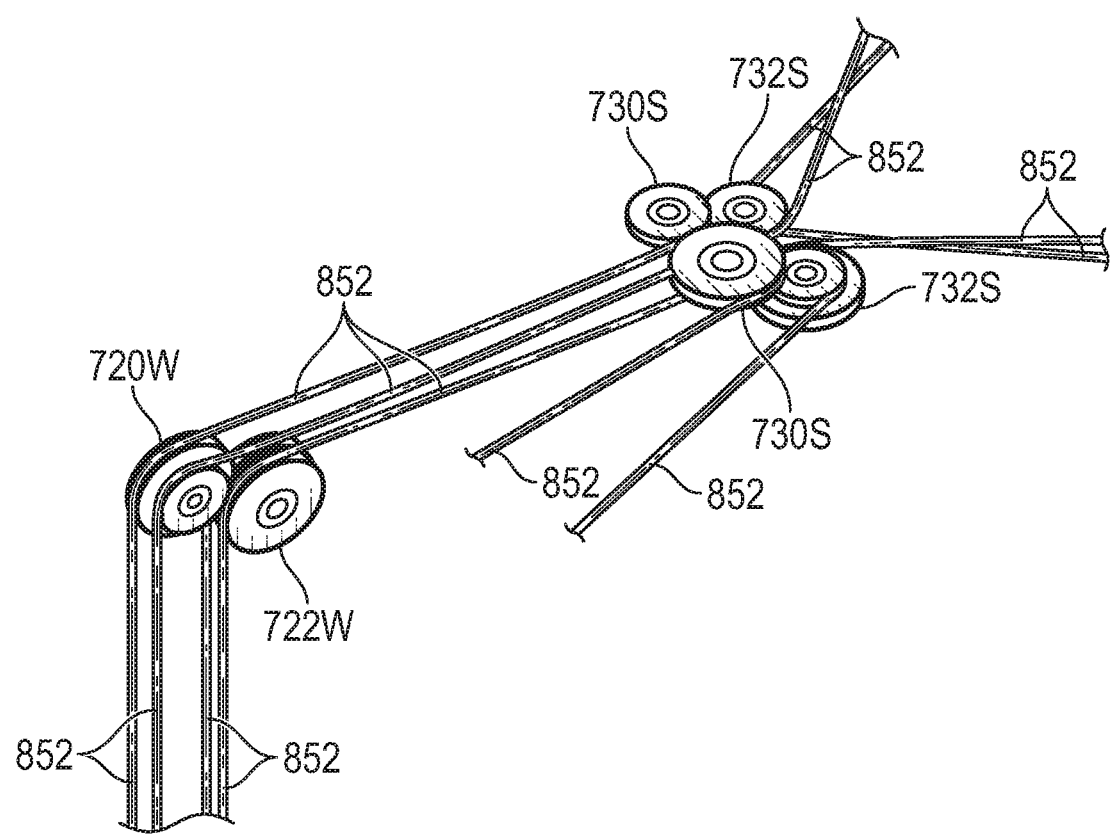
FIG. 9 is an illustrative partial perspective view perspective of showing the arrangement of the first and second sets of steering guide pulleys and the first and second sets of waterfall guide pulleys of FIG. 8.

FIG. 9 is an illustrative partial perspective view of showing the arrangement of the first and second sets of steering guide pulleys 730S, 732S and the first and second sets of waterfall guide pulleys 720W, 722W of FIG. 8. Rotational axes of the steering, pulleys 730S, 732S are perpendicular to rotational axes of the waterfall pulleys 720W, 722W. The steering pulleys 730S, 732S act to guide cables 852 operably coupled to drive elements (not shown) to associated waterfall pulleys 720W, 722W which guide the cables 852 into alignment axial alignment with the shaft (not shown).

Figure 10:
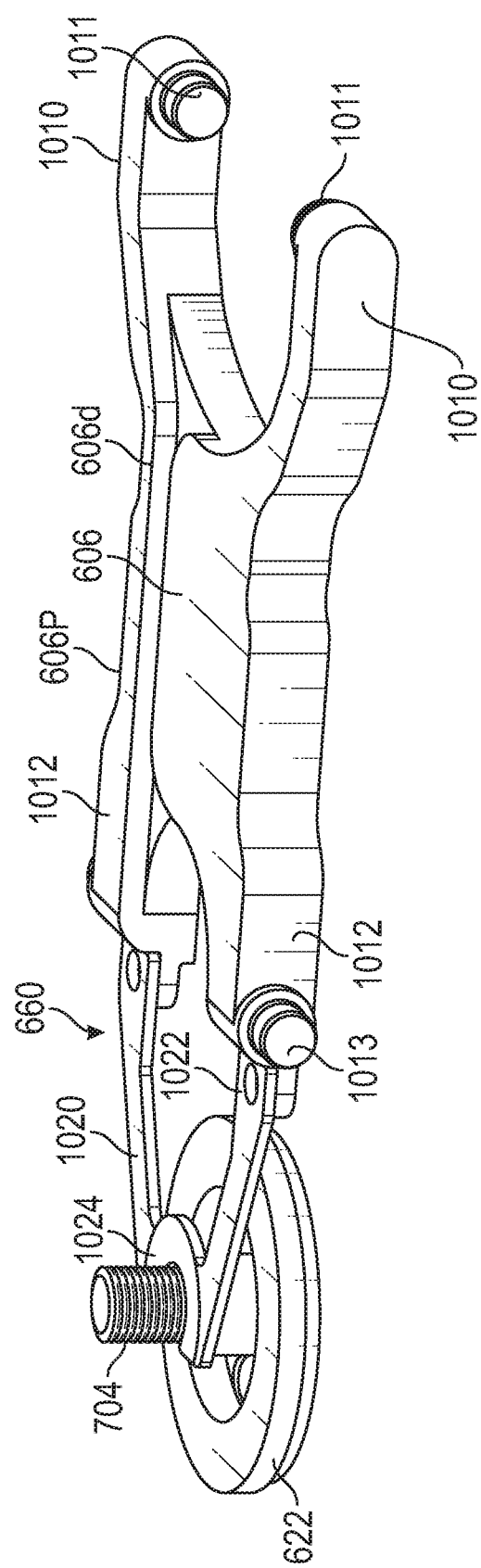
FIG. 10 is an illustrative perspective view of a first embodiment of the lower second side link and flexure beam and sensor assembly of FIGS. 6A-6C.

FIG. 10 is an illustrative perspective view of a first embodiment of the lower second side link 606 and flexure beam 660 and sensor 662 assembly of FIGS. 6A-6C. A distal end portion 606d of the side link 606 includes a distal clevis 1010 with inward facing pivot joint pins 1011 for pivotally mounting the shaft (not shown). A proximal end portion 606p of the side link 606 includes a proximal clevis 1012 with outward facing pivot joint pins 1013 for rotatable mounting at the second pivot joint 614 described above. The flexure beam 660 includes first and second rigid arms 1020, 1022 each coupled having a respective distal end coupled to a different one of the arms of the distal clevis 1012. The flexure beam 660 includes a cross member 1024 integrally secured to respective proximal ends of the first and second arms 1020, 1022. The first and second arms 1020 1022 have rectangular cross-section. The cross member 1024 is operatively coupled to the secured upstanding sensor beam 704. In some embodiments, axial stiffness along an axis of the upstanding sensor beam 704 stiffness is determined based upon bending stiffness of the flexure beam 660, stiffness of the sensor diaphragm 702 and length of the flexure beam 660. In some embodiments, the flexure beam 660 and the diaphragm 702 may be configured to provide an axial stiffness along an axis of the upstanding beam 704 such that the effective stiffness of the instrument along the axis 411 is tuned in such a way that it improves the stability of the teleoperation of the instrument in the presence of force feedback. For those skilled in the art of designing system teleoperation with force feedback and controls will be readily apparent the impact of effective stiffness of the end effector on the stability of the system when interacting with the environment. This configuration provides the ability to tune the stiffness along the axis 411 without compromising the ability to decouple cable forces from the forces $F_H$ applied on the end effector 454.

Figure 11:
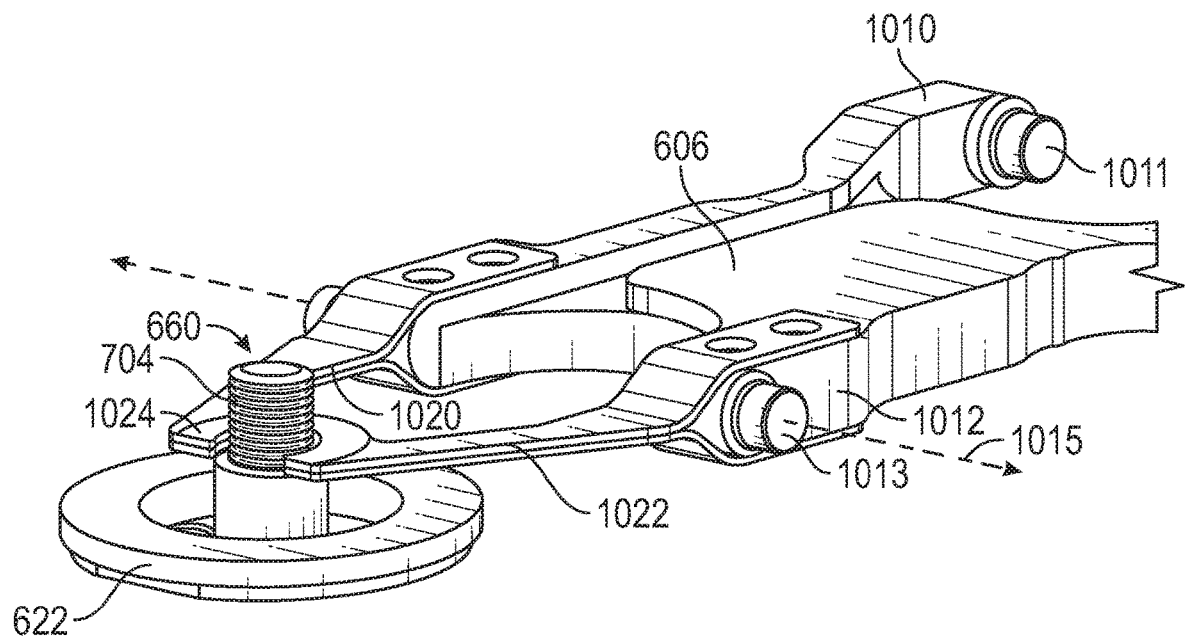
FIG. 11 an illustrative perspective partial view of a second embodiment of the lower second side link and flexure beam and sensor assembly of FIGS. 6A-6C.

FIG. 11 an illustrative perspective partial view of a second embodiment of the lower second side link 606 and flexure beam 660 and sensor 662 assembly of FIGS. 6A-6C. The flexure beam has a planar contour and is mounted such that a plane of the flexure beam passes through the second pivot joint axis 515. The flexure beam has a lateral axis 1015 that is colinear with the second pivot joint axis and has a longitudinal axis (not shown) that is aligned with the second side link longitudinal axis 506A when in rest position, so that when vertical motion of the proximal tool controller 440 causes minimal side to side deflection of the post 704. The diaphragm sensor 662 is designed to measure deflection of 704 in the vertical direction, so minimizing the side to side deflection of 704 is beneficial in terms of the magnitude of the side deflection/load the diaphragm sensor has to reject. This embodiment shows an alternative way to achieve this alignment and reduces the complexity of the parts and manufacturability.

Figure 12:
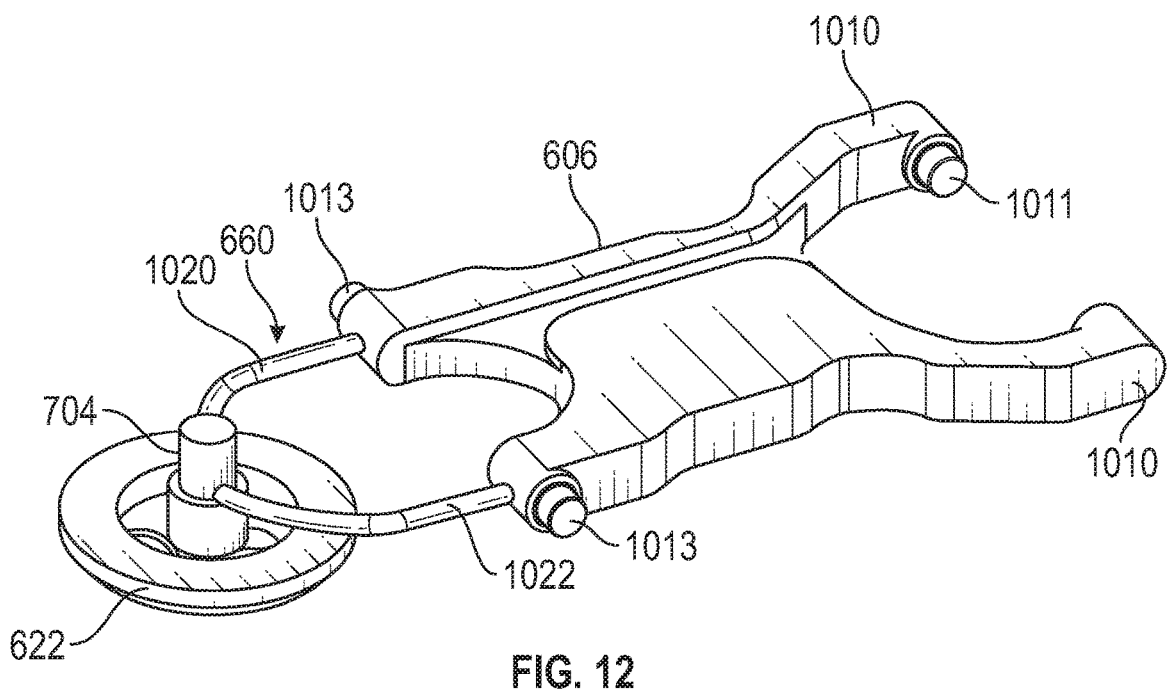
FIG. 12 an illustrative perspective view of a third embodiment of the lower second side link and flexure beam and sensor assembly of FIGS. 6A-6C.

FIG. 12 an illustrative perspective view of a third embodiment of the lower second side link 606 and flexure beam 660 and sensor 662 assembly of FIGS. 6A-6C. The first and second rigid arms 1020 1022 have circular cross-section. The third embodiment has advantages like those described above for the second embodiment.

The above description is presented to enable any person skilled in the art to create and use a surgical tool having a shaft having a proximal end portion suspended from a tool controller and having an end effector secured to a distal end portion thereof. The shaft is pivotally secured to a four-bar linkage structure at the tool controller to direct cable forces imparted to cables extending within the shaft between the tool controller and the end effector, while decoupling the cable forces from clinical axial forces imparted to the shaft due to contact between the shaft and anatomical tissue. Various modifications to the embodiments will be readily apparent to those skilled in the art, and the generic principles defined herein may be applied to other embodiments and applications without departing from the scope of the invention.

In view of the description herein it can be seen that any mechanical device that performs the function of the 4-bar linkage can be substituted for the 4-bar linkage. For example, a single rocking link between the chassis and the shaft that resists the cable forces might be used, as long as the shaft is constrained to movement along the shaft center axis, and as long cable length is not changed as the shaft moves with reference to the tool chassis.

And in view of the description herein it can be seen that other optional spring arrangements can be used to provide the necessary vertical resilient forces on shaft 410 along shaft center axis 411 in the proximal direction, the distal direction, or in both the proximal and distal directions. For example, one or more springs could be coupled directly to the shaft so that the shaft is held in a neutral position and the desired proximal, distal, or both proximal and distal resilient forces are imparted to the shaft.

And further in view of the description herein it can be seen that the force sensor may be in various positions with reference to the side links of the 4-bar linkage (or its equivalent). For example, as described herein the bottom side link and force sensor beam act together as a class 1 lever, but in optional embodiments they may be positioned as a class 2 lever. And, in other optional embodiments the force sensor beam may be coupled to the top side link of the 4-bar linkage.

And still further in view of the description herein it can be seen that cables may optionally be driven by drive inputs other than capstans. For example, optional linear drive members may be coupled to the proximal ends of the cables, and such linear drive members may be driven by lead screws or direct engagement with counterpart linear actuators.

In the preceding description, numerous details are set forth for the purpose of explanation. However, one of ordinary skill in the art will realize that the embodiments in the disclosure might be practiced without the use of these specific details. In other instances, well-known processes are shown in block diagram form in order not to obscure the description of the invention with unnecessary detail. Identical reference numerals may be used to represent different views of the same or similar item in different drawings. Thus, the foregoing description and drawings of embodiments in accordance with the present invention are merely illustrative of the principles of the invention. Therefore, it will be understood that various modifications can be made to the embodiments by those skilled in the art without departing from the scope of the invention, which is defined in the appended claims.

What is claimed is:

1. A surgical tool comprising:
   a chassis;
   a shaft including a proximal end portion and a distal end portion, the shaft having a longitudinal shaft center axis extending between the proximal end portion and the distal end portion;
   an end effector coupled to the distal end portion of the shaft;
   a linkage including a frame link coupled to the chassis, a coupler link coupled to the proximal end portion of the shaft, a first side link pivotally coupled to the frame link and pivotally coupled to the coupler link at a first pivot joint to rotate about a first pivot axis, and a second side link pivotally coupled to the frame link and pivotally coupled to the coupler link at a second pivot joint to rotate about a second pivot axis, the second pivot joint being different than the first pivot joint, and first pivot axis being different than the second pivot axis;
a first cable drive member coupled to the chassis;
a first distal pulley coupled to the coupler link;
a first proximal pulley coupled to the chassis; and
a first cable including a proximal end portion secured to the first cable drive member, a distal end portion extending within the shaft parallel to the longitudinal shaft center axis, and an intermediate segment engaging the first distal pulley and the first proximal pulley;
wherein the first distal pulley and the first proximal pulley are positioned to route the first cable between the first cable drive member and the proximal end portion of the shaft and to isolate a cable force imparted to the first cable by the first cable drive member from an axial force imparted to the end effector in a direction parallel to the longitudinal shaft center axis.

2. The surgical tool of claim 1, wherein:
the surgical tool further comprises a second cable drive member, a second distal pulley, a second proximal pulley, and a second cable;
the second cable drive member is coupled to the chassis;
the second distal pulley is coupled to the coupler link;
the second proximal pulley is coupled to the chassis;
the second cable includes a proximal end portion operably coupled to the second cable drive member, a distal end portion extending within the shaft parallel to the longitudinal shaft center axis, and an intermediate segment engaging the second distal pulley and the second proximal pulley; and
the second distal pulley and the second proximal pulley are positioned to route the second cable between the second cable drive member and the proximal end portion of the shaft to isolate a cable force imparted to the second cable by the second cable drive member from the axial force imparted to the end effector in a direction parallel to the longitudinal shaft center axis.

3. The surgical tool of claim 1, wherein:
the first distal pulley rotates about a first distal pulley rotation axis;
the first proximal pulley rotates about a first proximal pulley rotation axis; and
the first distal pulley rotation axis is nonparallel to the first proximal pulley rotation axis.

4. The surgical tool of claim 1, wherein:
the first side link includes a proximal portion and a distal portion;
the proximal portion of the first side link is rotatably coupled to the frame link at a third pivot axis;
the distal portion of the first side link is rotatably coupled to the coupler link at the first pivot axis;
the first proximal pulley rotates about a first proximal pulley rotation axis;
the first distal pulley rotates about a first distal pulley rotation axis; and
a distance between the third pivot axis and the first pivot axis matches a distance between the first distal pulley rotation axis and the first proximal pulley rotation axis.

5. The surgical tool of claim 4, wherein:
the surgical tool further comprises a second cable drive member, a second distal pulley, a second proximal pulley, and a second cable;
the second cable drive member is coupled to the chassis;
the second distal pulley is coupled to the coupler link and rotates about a second distal pulley rotation axis;
the second proximal pulley is coupled to the chassis and rotates about a second proximal pulley rotation axis;
the second cable includes a proximal end portion secured to the second cable drive member, a distal end portion extending within the shaft parallel to the longitudinal shaft center axis, and an intermediate segment engaging the second distal pulley and engaging the second proximal pulley;
the second side link includes a proximal portion and a distal portion;
the proximal portion of the second side link is rotatably coupled to the frame link at a fourth pivot axis;
the distal portion of the second side link is rotatably coupled to the coupler link at the second pivot axis; and
a distance between the fourth pivot axis and the second pivot axis matches a distance between the second distal pulley rotation axis and the second proximal pulley rotation axis.

6. The surgical tool of claim 1, wherein:
the surgical tool further comprises a force sensor operatively coupled to the linkage; and
an axial force imparted on the shaft causes the shaft to be displaced axially a first distance and a portion of the force sensor to be displaced axially a second distance corresponding to the first distance.

7. A surgical tool comprising:
a linkage including a frame link, a coupler link, a first side link rotatably coupled to the frame link at a first pivot joint and to the coupler link at a third pivot joint to rotate about a first pivot axis, and a second side link rotatably coupled to the frame link at a second pivot joint and to the coupler link at a fourth pivot joint to rotate about a second pivot axis, the second pivot axis being different than the first pivot axis, the third pivot joint being different than the fourth pivot joint;
a shaft including a proximal end portion and a distal end portion, with an axial direction of the shaft defined by a length between the proximal and distal end portions of the shaft;
an end effector coupled to the distal end portion of the shaft; and
a sensor operatively coupled to the linkage or to the shaft;
wherein the proximal end portion of the shaft includes the coupler link; and
wherein an axial force imparted on the shaft causes the shaft to be displaced axially a first distance and a portion of the sensor to be displaced axially a second distance corresponding to the first distance.

8. The surgical tool of claim 7, wherein:
the surgical tool further comprises a first proximal pulley, a first distal pulley, a first cable drive member, and a first cable;
the first proximal pulley is coupled to the frame link to rotate about a rotation axis of the first proximal pulley;
the first distal pulley is coupled to the coupler link to rotate about a rotation axis of the first distal pulley;
the first cable drive member is coupled to the frame link; and
the first cable includes a proximal end portion secured to the first cable drive member, a distal end portion secured to the end effector, and an intermediate segment engaging the first proximal pulley and the first distal pulley;
the first proximal pulley and the first distal pulley are arranged to cooperatively guide the intermediate segment of the first cable parallel to the first and second side links during rocking motion of the linkage.

9. The surgical tool of claim 8, wherein:
the surgical tool further comprises a second proximal pulley, a second distal pulley, and a second cable;
the second proximal pulley is rotatably coupled to the frame link between the first and second side links and rotates about a rotation axis of the second proximal pulley;
the second distal pulley is rotatably coupled to the coupler link between the first and second side links and rotates about a rotation axis of the second distal pulley;
the second cable engages the second proximal pulley, engages the second distal pulley, and extends within the shaft parallel to a shaft longitudinal axis;
the rotation axis of the first proximal pulley and the rotation axis of the second proximal pulley are offset from one another by a pulley lateral offset amount;
the rotation axis of the first proximal pulley and the rotation axis of the second proximal pulley are offset from one another by a pulley vertical offset amount;
the rotation axis of the first distal pulley and a rotation axis of the second distal pulley are offset from one another by the pulley lateral offset amount;
the rotation axis of the first distal pulley and a rotation axis of the second distal pulley are offset from one another by the pulley vertical offset amount;
the rotation axis of the first distal pulley is laterally offset from the rotation axis of the first proximal pulley by the lateral offset length;
the rotation axis of the second distal pulley is laterally offset from the rotation axis of the second proximal pulley by the lateral offset length; and
the second proximal pulley and the second distal pulley are positioned to cooperatively guide the intermediate segment of the second cable parallel to the first and second side links during the rocking motion of the linkage.

10. The surgical tool of claim 8, wherein:
the surgical tool further comprises a second proximal pulley, a second distal pulley, a second cable drive member, and a second cable;
the second proximal pulley is rotatably coupled to the frame link to rotate about a rotation axis of the second proximal pulley between the first side link and the second side link and offset from the first proximal pulley;
the first proximal pulley has a diameter, and the second proximal pulley has a diameter different from the diameter of the first proximal pulley;
the second distal pulley is rotatably coupled to the coupler link to rotate about a rotation axis of the second distal pulley between the first side link and the second side link and coaxial with the rotation axis of the first distal pulley;
the rotation axis of the first distal pulley is laterally offset from the rotation axis of the first proximal pulley;
the rotation axis of the second distal pulley is laterally offset from the rotation axis of the second proximal pulley;
the second cable includes a proximal end portion secured to the second cable drive member, a distal end portion secured to the end effector, and an intermediate segment engaging the second proximal pulley and the second distal pulley; and
the second proximal pulley and the second distal pulley are arranged to cooperatively guide the intermediate segment of the second cable parallel to the first and second side links during the rocking motion of the linkage.

11. The surgical tool of claim 10, wherein:
the first distal pulley has a diameter, and the second distal pulley has a diameter different from the diameter of the first distal pulley.

12. The surgical tool of claim 7, wherein:
an insertion axis stiffness for the shaft along the axial direction of the shaft is in a range of 5-50 N/mm; and
the sensor includes a force sensor configured to sense force within a range of approximately ±20 N.

13. The surgical tool of claim 7, wherein:
the sensor includes a flexure and a flexible diaphragm; and
the flexure is operatively coupled to impart a force to the flexible diaphragm indicative of the axial force imparted to the shaft.

14. The surgical tool of claim 7, further comprising:
a first proximal pulley coupled to the frame link; and
a first distal pulley coupled to the coupler link;
wherein the first distal pulley rotates about a first distal pulley rotation axis,
wherein the first proximal pulley rotates about a first proximal pulley rotation axis, and
wherein the first distal pulley rotation is nonparallel to the first proximal pulley rotation axis.

15. The surgical tool of claim 7, wherein:
the sensor is a coil inductive displacement sensor.

16. The surgical tool of claim 7, wherein:
the sensor includes an inductive coil, a sensor shaft moveably coupled to the inductive coil, and a magnet coupled the sensor shaft;
an axial force imparted on the shaft causes the shaft to be displaced axially a first distance; and
the axial force imparted on the shaft causes the sensor shaft and magnet to be displaced axially a second distance within the inductive coil corresponding to the first distance.

17. A surgical tool comprising:
a chassis;
a cable drive element mounted in the chassis;
a shaft;
a linkage comprising a first pair of opposite links and a second pair of opposite links,
a first link of the first pair of opposite links being coupled to the chassis, and
a second link of the first pair of opposite links being coupled to the shaft,
a first link of the second pair of opposite links being coupled between the first and second links of the first pair of opposite links and pivotally coupled to the shaft at a first pivot joint to rotate about a first pivot axis, and
a second link of the second pair of opposite links being coupled between the first and second links of the first pair of opposite links and pivotally coupled to the shaft at a second pivot joint to rotate about a second pivot axis, the first pivot joint being different than the second pivot joint and the first pivot axis being different than the second pivot axis;
a cable routed from the cable drive element via a path parallel to the second pair of opposite links of the linkage and through the shaft; and
a sensor operatively coupled to the linkage;
wherein an axial force imparted on the shaft causes the shaft to be displaced axially a first distance and a portion of the sensor to be displaced axially a second distance corresponding to the first distance.

18. The surgical tool of claim 17, further comprising:
a beam coupled between the first link of the second pair of opposite links of the linkage and the sensor.

19. The surgical tool of claim 18, wherein:
the beam is a resilient, flexible beam.

20. The surgical tool of claim 17, wherein:
the sensor is a coil inductive displacement sensor.

21. The surgical tool of claim 17, wherein:
the sensor includes an inductive coil, a sensor shaft moveably coupled to the inductive coil, and a magnet coupled the sensor shaft; and
an axial force imparted on the shaft, causes the shaft to be displaced axially a first distance, and the sensor shaft and magnet to be displaced axially a second distance within the inductive coil corresponding to the first distance.

\* \* \* \* \*